US010080909B2

(12) United States Patent
Brachman et al.

(10) Patent No.: US 10,080,909 B2
(45) Date of Patent: *Sep. 25, 2018

(54) APPARATUS AND METHOD FOR LOADING RADIOACTIVE SEEDS INTO CARRIERS

(71) Applicant: GT MEDICAL TECHNOLOGIES, INC., Mesa, AZ (US)

(72) Inventors: David Brachman, Phoenix, AZ (US); Evan Fram, Phoenix, AZ (US); Heyoung McBride, Phoenix, AZ (US); Peter Nakaji, Phoenix, AZ (US); Theresa Thomas, Gilbert, AZ (US); Emad Youssef, Peoria, AZ (US)

(73) Assignee: GT Medical Technologies, Inc., Mesa, AZ (US)

(*) Notice: Subject to any disclaimer, the term of this patent is extended or adjusted under 35 U.S.C. 154(b) by 58 days.

This patent is subject to a terminal disclaimer.

(21) Appl. No.: 15/223,806

(22) Filed: Jul. 29, 2016

(65) Prior Publication Data

US 2017/0021191 A1 Jan. 26, 2017

Related U.S. Application Data

(63) Continuation of application No. 14/696,293, filed on Apr. 24, 2015, now Pat. No. 9,403,033.

(51) Int. Cl.
*A61N 5/10* (2006.01)
(52) U.S. Cl.
CPC ...... *A61N 5/1007* (2013.01); *A61N 2005/101* (2013.01); *A61N 2005/1009* (2013.01); *A61N 2005/1024* (2013.01)

(58) Field of Classification Search
CPC ............... A61N 5/1001; A61N 5/1007; A61N 2005/1008–2005/1012; A61N 2005/1019–2005/1024; A61M 37/0069
See application file for complete search history.

(56) References Cited

U.S. PATENT DOCUMENTS

| D244,393 S | 5/1977 | Collica et al. |
| 4,706,652 A | 11/1987 | Horowitz |
| 4,754,745 A | 7/1988 | Horowitz |
| 4,946,435 A | 8/1990 | Suthanthiran et al. |
| 5,030,195 A | 7/1991 | Nardi |
| D381,080 S | 7/1997 | Ohata |

(Continued)

FOREIGN PATENT DOCUMENTS

| DE | 613 528 | 5/1935 |
| EP | 0 292 630 B1 | 8/1995 |

(Continued)

OTHER PUBLICATIONS

Cole, P.D., et al., "A comparative long-term assessment of four soft tissue supplements". Anesthetic Surg J. 31(6). 674-681, 2011.

(Continued)

*Primary Examiner* — Thaddeus Cox
(74) *Attorney, Agent, or Firm* — Knobbe, Martens, Olson & Bear LLP

(57) ABSTRACT

An apparatus and method for loading brachytherapy carriers with radioactive seeds in order to implement brachytherapy treatment protocols with more precise and predictable dosimetry. These apparatuses and methods enable a medical team to create a radionuclide carrier for each patient and tumor reliably, reproducibly and efficiently.

17 Claims, 17 Drawing Sheets

(56) References Cited

U.S. PATENT DOCUMENTS

| | | |
|---|---|---|
| 5,772,574 A | 6/1998 | Nanko |
| 5,803,895 A | 9/1998 | Kronholz et al. |
| 5,840,008 A | 11/1998 | Klein et al. |
| 5,871,708 A | 2/1999 | Park et al. |
| D408,957 S | 4/1999 | Sandor |
| 5,967,966 A | 10/1999 | Kronholz et al. |
| 5,997,842 A | 12/1999 | Chen |
| 6,017,482 A | 1/2000 | Anders et al. |
| D420,452 S | 2/2000 | Cardy |
| D420,745 S | 2/2000 | Cardy |
| D420,746 S | 2/2000 | Cardy |
| 6,129,670 A | 10/2000 | Burdette et al. |
| D443,061 S | 5/2001 | Bergstrom et al. |
| 6,248,057 B1 | 6/2001 | Mavity et al. |
| 6,327,490 B1 | 12/2001 | Spetz |
| 6,358,195 B1 | 3/2002 | Green et al. |
| 6,360,116 B1 | 3/2002 | Jackson et al. |
| 6,385,477 B1 | 5/2002 | Werner et al. |
| 6,450,937 B1 | 9/2002 | Mercereau et al. |
| 6,471,631 B1 | 10/2002 | Slater et al. |
| 6,512,943 B1 | 1/2003 | Kelcz |
| 6,712,508 B2 | 3/2004 | Nilsson et al. |
| D488,864 S | 4/2004 | Fago et al. |
| 6,787,042 B2 | 9/2004 | Bond et al. |
| 7,011,619 B1 | 3/2006 | Lewis |
| D561,896 S | 2/2008 | Jones |
| D580,056 S | 11/2008 | Orthner |
| D580,057 S | 11/2008 | Ramadani |
| 7,776,310 B2 | 8/2010 | Kaplan |
| 8,039,790 B2 | 10/2011 | Cho et al. |
| D657,474 S | 4/2012 | Dona |
| D680,649 S | 4/2013 | Jagger et al. |
| D681,210 S | 4/2013 | Beiriger et al. |
| D681,812 S | 5/2013 | Farris et al. |
| D681,813 S | 5/2013 | Jagger et al. |
| D686,341 S | 7/2013 | Nakaji et al. |
| D686,744 S | 7/2013 | Nakaji et al. |
| D686,745 S | 7/2013 | Nakaji et al. |
| D686,746 S | 7/2013 | Nakaji et al. |
| D686,747 S | 7/2013 | Nakaji et al. |
| D686,748 S | 7/2013 | Nakaji et al. |
| D687,568 S | 8/2013 | Nakaji et al. |
| D687,966 S | 8/2013 | Nakaji et al. |
| D687,967 S | 8/2013 | Nakaji et al. |
| 8,600,130 B2 | 12/2013 | Eriksson Järliden |
| 8,605,966 B2 | 12/2013 | Eriksson Järliden |
| 8,825,136 B2 | 9/2014 | Giller et al. |
| 8,876,684 B1 | 11/2014 | Nakaji et al. |
| 8,939,881 B2 | 1/2015 | Nakaji et al. |
| 8,974,364 B1 | 3/2015 | Nakaji et al. |
| 9,022,915 B2 | 5/2015 | Nakaji et al. |
| 9,403,033 B1 | 8/2016 | Brachman |
| 9,409,038 B2 | 8/2016 | Nakaji et al. |
| 9,492,683 B2 | 11/2016 | Brachman et al. |
| 9,526,463 B2 | 12/2016 | Brachman et al. |
| 9,545,525 B2 | 1/2017 | Nakaji et al. |
| 2001/0044567 A1 | 11/2001 | Zamora et al. |
| 2002/0058854 A1 | 5/2002 | Creed et al. |
| 2003/0045769 A1 | 3/2003 | Kalas et al. |
| 2003/0088141 A1 | 5/2003 | Terwilliger et al. |
| 2003/0130573 A1 | 7/2003 | Yu et al. |
| 2003/0208096 A1 | 11/2003 | Tam |
| 2004/0109823 A1 | 6/2004 | Kaplan |
| 2004/0116767 A1 | 6/2004 | Lebovic et al. |
| 2004/0242953 A1 | 12/2004 | Good |
| 2005/0035310 A1 | 2/2005 | Drobnik et al. |
| 2005/0244045 A1 | 11/2005 | Eriksson |
| 2006/0015030 A1 | 1/2006 | Poulin et al. |
| 2006/0063962 A1 | 3/2006 | Drobnik et al. |
| 2006/0173236 A1 | 8/2006 | White et al. |
| 2006/0235365 A1 | 10/2006 | Terwilliger |
| 2007/0225544 A1 | 9/2007 | Vance et al. |
| 2008/0004714 A1 | 1/2008 | Lieberman |
| 2008/0146861 A1 | 6/2008 | Murphy et al. |
| 2008/0221384 A1 | 9/2008 | Chi Sing et al. |
| 2009/0012347 A1 | 1/2009 | Helle |
| 2009/0131735 A1 | 5/2009 | Drobnik et al. |
| 2009/0253950 A1 | 10/2009 | Rapach et al. |
| 2009/0271715 A1 | 10/2009 | Tumuluri |
| 2010/0056908 A1 | 3/2010 | Giller et al. |
| 2010/0200778 A1 | 8/2010 | Drobnik et al. |
| 2010/0228074 A1 | 9/2010 | Drobnik et al. |
| 2010/0268015 A1 | 10/2010 | Drobnik et al. |
| 2010/0288916 A1 | 11/2010 | Cho et al. |
| 2010/0324353 A1 | 12/2010 | Helle |
| 2011/0013818 A1 | 1/2011 | Eriksson Järliden |
| 2011/0206252 A1 | 8/2011 | Eriksson Järliden |
| 2013/0131434 A1 | 5/2013 | Nakaji et al. |
| 2013/0338423 A1 | 12/2013 | Nakaji et al. |
| 2014/0275715 A1 | 9/2014 | Brachmann et al. |
| 2014/0316187 A1 | 10/2014 | Nakaji et al. |
| 2015/0057487 A1 | 2/2015 | Nakaji et al. |
| 2015/0140535 A1 | 5/2015 | Geri et al. |
| 2015/0196778 A1 | 7/2015 | Nakaji et al. |
| 2015/0321024 A1 | 11/2015 | Nakaji et al. |
| 2015/0367144 A1 | 12/2015 | Flynn et al. |
| 2017/0120073 A1 | 5/2017 | Brachman et al. |
| 2017/0215824 A1 | 8/2017 | Brachman et al. |
| 2017/0252575 A1 | 9/2017 | Nakaji et al. |

FOREIGN PATENT DOCUMENTS

| | | |
|---|---|---|
| EP | 0 906 769 A2 | 4/1999 |
| JP | S52-9424 | 7/1975 |
| JP | H09-028810 | 4/1997 |
| JP | 2001-266903 | 9/2001 |
| JP | 3095304 | 7/2003 |
| JP | 2007-512112 | 5/2007 |
| JP | 2009-515603 | 4/2009 |
| JP | 2010-536529 | 12/2010 |
| WO | WO 2007/106531 A1 | 9/2007 |
| WO | WO 2012/100206 A2 | 7/2012 |
| WO | WO 2012/149580 A1 | 11/2012 |
| WO | WO 2016/171961 | 10/2016 |
| WO | WO 2016/179420 | 11/2016 |

OTHER PUBLICATIONS

International Search Report; International Application No. PCT/US2012/035907, dated Sep. 26, 2012; 3 pages.

International Search Report; International Application No. PCT/US2012/035909, dated Aug. 30, 2012; 3 pages.

Crepeau, R.H., et al., "Image Processing of Imperfect Protein Arrays: Sectioned Crystals and Tubulin Sheets and Rings". Elec. Microsc. Soc. Amer. Proc. 40:84-87, 1982.

Crepeau, R.H., et al., "Reconstruction of imperfectly ordered zinc-induced tubulin sheets using cross-correlation and real space averaging". Ultramicroscopy, 6, 7-18, 1981.

Dagnew, E., et al., "Management of newly diagnosed single brain metastasis using resection and permanent iodine-125 seeds without initial whole-brain radiotherapy: a two institution experience". Neurosurg Focus. 15; 22(3):E3, 2007.

Delaney, T.F., et al., "Intraoperative dural irradiation by customized 192I iridium and 90 Yttrium brachytherapy plaques". Int. J. Radiat Oncol Biol Phys. 57(1): 239-245, 2003.

Gutin, P.H., et al., "A coaxial catheter system for afterloading radioactive sources for the interstitial irradiation of brain tumors. Technical note". J. Neurosurg 56: 734-735, 1982.

Gutin, P.H., et al., "Brachytherapy of recurrent tumors of the skull base and spine with iodine-125 sources". Neurosurgery 20:938-945, 1987.

Hamilton, A.J., et al., "The use of gold foil wrapping for radiation protection of the spinal cord for recurrent tumor therapy". Int. J. Radiat Oncol Biol Phys. 32(2):507-511, 1995.

Hilaris, B.S., et al., "Interstitial irradiation for unresectable carcinoma of the lung". Ann Thoracic Surg; 20:491-500, 1975.

Hilaris, B.S., et al., "Intraoperative radiotherapy in stage I and II lung cancer". Semin Surg Oncol. 3:22-32, 1987.

Huang, K., et al., "Surgical resection and permanent iodine-125 brachytherapy for brain metastases". J. Neurooncol. 91:83-93, 2009.

(56) References Cited

OTHER PUBLICATIONS

Jenkins, H.P., et al., "Clinical and experimental observations on the use of a gelatin sponge or foam". Surg 20:124-132, 1946.

Kneschaurek, P. et al., "Die Flabmethode Zur Intraoperativen Bestrahlung. Öthe Flab-Method for Intraoperative Radiation Therapy", Strahlentherapie and Oknologie, Urban Und Vogel, Muenchen, DE, vol. 171, No. 2; Feb. 1, 1995, pp. 61-69, XP000610565, ISSN:0179-7158.

Marchese, M.J., et al., "A versatile permanent planar implant technique utilizing iodine-125 seeds imbedded in gelfoam". Int J Radiat Oncol Biol Phys 10:747-751, 1984.

Murphy, M.K., et al., "Evaluation of the new cesium-131 seed for use in low-energy x-ray brachytherapy". Med Phy 31(6): 1529-1538, Jun. 2004.

Nori, D., et al., "Intraoperative brachytherapy using Gelfoam radioactive plaque implants for resected stage III non-small-cell lung cancer with positive margin: A pilot study". J Surg Oncol. 60:257-261, 1995.

Parashar, B., et al., "Cesium-131 permanent seed brachytherapy: Dosimetric evaluation and radiation exposure to surgeons, radiation oncologists, and staff". Brachytherapy. 10:508-511, 2011.

Patel, S., et al., "Permanent iodine-125 interstitial implants for the treatment of recurrent Glioblastoma Multiforme". Neurosurgery 46 (5) 1123-1128, 2000.

Rivard, M.J., "Brachytherapy dosimetry parameters calculated for a 131 Cs source". Med Phys. 34(2): 754-765, 2007.

Rogers, C.L., et al., "Surgery and permanent 125-1 seed paraspinal brachytherapy for malignant tumors with spinal cord compression". Int. J. Radial Oncol Biol Phys. 54(2): 505-513, 2002.

Wernicke, A.G., et al., "Feasibility and safety of Gliasite brachytherapy in the treatment of CNS tumors following neurosurgical resection". J. Cancer Res Ther. 6(1), 65-74, Jan.-Mar. 2010.

Office Action dated Apr. 2, 2015; European Patent Application No. 12724426.7; 5 pages.

Office Action dated Oct. 30, 2015; European Patent Application No. 12724426.7; 4 pages.

Office Action dated Feb. 9, 2016; Japanese Application No. 2014-508190; 5 pages including english translation.

International Search Report; International Application No. PCT/US2016/031035; filed May 5, 2016; 15 pages.

International Search Report and Written Opinion; International Application No. PCT/US2016/027143, filed Apr. 12, 2016; dated Aug. 25, 2016; 7 pages.

Decision of Rejection dated Feb. 4, 2016, Japanese Patent Application No. 2014-508190 with English Translation; 4 pages.

Search and Examination Report; Application No. P1140/13; Filed on Oct. 24, 2013 (PCT dated Apr. 30, 2012); 10 pages.

Ewersten, et al., "Biopsy Guided by Real-Time Sonography Fused with MRI: A Phantom Study", American Journal of Roentgenology. 2008; 190: 1672-1674. 10.2214/AJR.07.2587.

Summons to Attend Oral Proceedings dated Aug. 18, 2017; European Application No. 12724426.7; 5 pages.

APPARATUS AND METHOD FOR LOADING RADIOACTIVE SEEDS INTO CARRIERS

PRIORITY CLAIM

This application is a continuation of U.S. patent application Ser. No. 14/696,293, filed on Apr. 24, 2015, now U.S. Pat. No. 9,403,033, entitled "APPARATUS AND METHOD FOR LOADING RADIOACTIVE SEEDS INTO CARRIERS". The disclosure of the foregoing application is hereby incorporated by reference in its entirety.

FIELD

The invention generally relates to improvements to radioactive brachytherapy.

BACKGROUND

Tumors in living organisms are highly variable in size, location and their amount of infiltration into normal tissues, and the variability of tumors in general make them very difficult to treat with a one-size fits all approach. Furthermore, the extent of tumors and/or void created upon debulking are typically not known until presented in the operating room. Thus the options necessary to effectively treat a tumor or tumor bed need to be quite diverse.

Brachytherapy involves placing a radiation source either into or immediately adjacent to a tumor. It provides an effective treatment of cancers of many body sites. Brachytherapy, as a component of multimodality cancer care, provides cost-effective treatment. Brachytherapy may be intracavitary, such as when treating gynecologic malignancies; intraluminal, such as when treating esophageal or lung cancers; external surface, such as when treating cancers of the skin, or interstitial, such as when treating various central nervous system tumors as well as extracranial tumors of the head and neck, lung, soft tissue, gynecologic sites, rectum, liver, prostate, penis and skin.

SUMMARY

The systems, methods, and devices described herein each have several aspects, no single one of which is solely responsible for its desirable attributes. Without limiting the scope of this disclosure, several non-limiting features will now be described briefly.

In one embodiment, an apparatus comprises a loader having a top surface, an opposing bottom surface, and a receiving surface therebetween, the loader further comprising: a loading bed configured to contain a radioactive seed carrier, the carrier comprising collagen and configured to contain a radioactive seed, the carrier having a first surface, and an opposing second surface; and a loading port through the receiving surface, the loading port defining a channel configured to receive an injection device. In one embodiment, the injection device comprises a distal end configured for insertion into the loading port, an injection channel configured to contain a radioactive seed, and a plunger having a first end comprising a longitudinal rod extending at least partially within the injection channel and a second end outside of the injection channel configured for engagement by a human operator in order to move the longitudinal rod within the injection channel. In one embodiment, the distal end of the injection device is configured for at least partial insertion into the loading port in order to move the radioactive seed out of the injection device into the carrier in response to pushing the second end of the plunger towards the distal end of the injection device.

BRIEF DESCRIPTION OF THE DRAWINGS

The principles of the present invention will be apparent with reference to the following drawings, in which like reference numerals denote like components.

DETAILED DESCRIPTION

Figure 1:
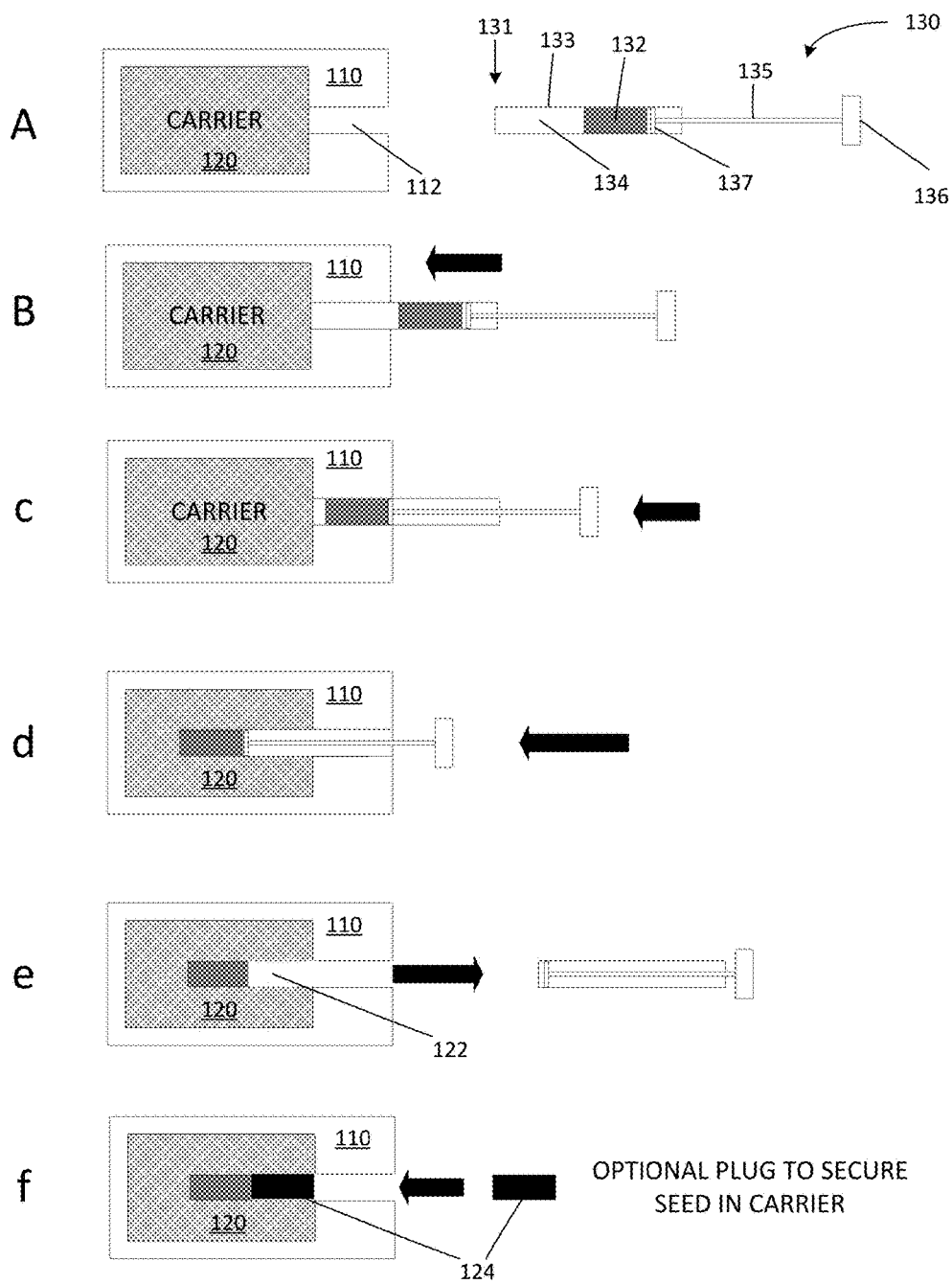
FIG. 1 is a cross-sectional diagram of a loader containing a carrier and an injector.

Although certain preferred embodiments and examples are disclosed below, inventive subject matter extends beyond the specifically disclosed embodiments to other alternative embodiments and/or uses and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Definitions

In order to facilitate an understanding of the systems and methods discussed herein, a number of terms are defined below. The terms defined below, as well as other terms used herein, should be construed to include the provided definitions, the ordinary and customary meaning of the terms, and/or any other implied meaning for the respective terms. Thus, the definitions below do not limit the meaning of these terms, but only provide exemplary definitions.

Tumor bed: an anatomical area where a tumor exists and/or an area surrounding a surgically removed tumor, such as a cranial cavity from which a tumor was surgically removed.

Brachytherapy: radiation treatment in which the source of radiation is placed close to the surface of the body, on the surface of the body, within the body, or in a tumor bed.

Seed: a radioactive material that is configured for delivery of radiation to a tumor and/or tumor bed. A seed may be in various shapes and sizes, such as cylinder, cone, sphere, pyramid, cube, prism, rectangular prism, triangular prism, and/or any combination of these or other shapes. While seeds are generally referred to herein as cylindrical, any other shape or size of seed may alternatively be used in the various systems and methods discussed herein. Seeds may comprise any combination of one or more multiple radioactive components, such as Cs 131, Ir 192, I 125, Pd 103, for example. Seeds may include a protective outer shell that partially or fully encases the radioactive material.

Carrier: a substrate that holds or contains a radioactive seed. Carriers may be configured for permanent implantation into a tumor bed, such as to provide radioactive energy to a tumor and/or area where a tumor has been removed in order to treat any remaining malignant tissue. Carriers can be composed of various materials and take on various shapes and sizes. Examples carriers, such as carriers having various sizes, shapes, configurations, etc., are included in the following patents, each of which is hereby incorporated by reference in its entirety and for all purposes:

U.S. patent application Ser. No. 14/322,785, filed Jul. 2, 2014, now U.S. Pat. No. 8,876,684, entitled "Dosimetrically Customizable Brachytherapy Carriers And Methods Thereof In The Treatment Of Tumors," and U.S. patent application Ser. No. 14/216,723, filed Mar. 17, 2014, publication No. 2014/0275715, entitled "Dosimetrically Customizable Brachytherapy Carriers And Methods Thereof In The Treatment Of Tumors."

Tile Carrier (also referred to as "Tile"): type of carrier that is planar and maintains a two-dimensional planar geometry when placed in a tumors bed.

Gore Carrier (also referred to as "Gore"): type of carrier that is 3-dimensional and conform to the treatment environment while maintaining the geometry necessary for an effective implant. In some embodiments, gores are initially planar and are reconfigured to take on a 3-dimensional shape, such as to form a hemispherical surface that may be placed into a similarly shaped tumor cavity.

Loader: a device that aids in placement of radioactive seeds in carriers, such as via injection of seeds into carriers. A loader, also referred to herein as a "loading device," may include multiple components, such as to hold a carrier in place and guide a delivery device, such as a needle or injector, into the carrier in order to place a seed at a precise location in the carrier. U.S. patent application Ser. No. 13/460,809, filed Apr. 30, 2012, now U.S. Pat. No. 8,939,881, entitled "Apparatus For Loading Dosimetrically Customizable Brachytherapy Carriers," which is hereby incorporated by reference in its entirety for all purposes, describes several embodiments of loaders. As discussed further herein, loaders may be operated manually, such as by human operators, or may be fully automated, such that carriers can be loaded with seeds using an automated process. Alternatively, loaders may be configured to be automated in part and require manual operation in part. Each loader includes a loading bed, which is a portion of the loader configured to receive one or more carriers (and/or a carrier cartridge that houses multiple carriers) for loading of one or more seeds into the one or more carriers.

Teletherapy: radiation treatment in which the source of the radiation is at a distance from the body.

High Z Materials: any element with an atomic number greater than 20, or an alloy containing such materials.

Hot material: a material that is Radioactive.

Cold material: a material low in radioactivity or not radioactive.

Dosimetry: a process of measurement and quantitative description of the radiation absorbed dose (rad) in a tissue or organ.

Tumor: an abnormal growth of tissue resulting from uncontrolled, progressive multiplication of cells. Tumors can be benign or malignant.

Example Embodiments

Described herein are various embodiments of loading devices and systems for enabling more precise, efficient, accurate, and/or convenient loading of radioactive seeds into radioactive carriers. The various loader configurations disclosed herein may be sterilizable single or multi-use devices for manual or automated loading (in real time or for preloading) of carriers (e.g., GammaTiles, GammaDots, GammaStars, or GammaGores provided by Gammatile, Inc.) with radioactive seeds such as I 125, Cs 131 or Pd 111 or other materials. The loaders may be constructed of metal, plastic or composite material, and manufactured by casting, molding, stamping, forming or 3D printing. Embodiments of the loaders may include shielding either by way of construction with a high Z material, or with other materials with a sufficient dimension (thickness) to provide the necessary dose attenuation for a user. Alternative embodiments may remain unshielded, and be made of materials suitable for the purpose including but not limited to tungsten, stainless steel, nylon or plastic.

FIG. 1 is a cross-sectional diagram of a loader 110 containing a carrier 120 and an injector 130. FIG. 1 illustrates an example process of loading a seed 132 into the carrier 120 using the injector 130 (also referred to as an "injection device" herein). In this example, the representations of the loader 110, carrier 120, injector 130, and seed 132 are shown repeatedly in different states as the seed 132 is loaded into the carrier 120 using the injector 130. The states are indicated by the illustrated "A"-"F" characters along the left margin of the figure. Similar labeling of states using characters in this same manner is used in other figures also to aid in illustrating example processes.

Beginning at state A, the injector 130 has been loaded with a seed 132 in preparation for injecting the seed 132 into the carrier 120, which is held in place in the loader 110. The seed 132 may be loaded into the injector 130 in various manners, some of which are discussed herein with reference to other figures. For example, in one embodiment the seed is dropped into an opening at the distal end 131 of the injector 130. In other embodiments, the seed is preloaded into the injector 130, such as might be received from a manufacturer of the injector 130, so that loading of the seed 132 into the injector 130 is not required by the individual that performs the process illustrated in FIG. 1 (as well as other similar processes discussed herein). In other embodiments, automated loading systems may be used, such as a magazine that automatically inserts a seed into an injection channel 134 of the injector 130. In one embodiment, seeds are sized to fit a channel similar to that of a syringe, such as a 17 gauge syringe channel. However, other sized seeds, either smaller, larger, different shape, etc., may be used in the embodiments discussed herein. For example, other sizes, shapes, dimensions, and characteristics of seeds, such as those provided in the various applications and patents incorporated by reference herein, may be used in the injection systems and methods discussed herein.

In the embodiment of FIG. 1, the injector 130 comprises a plunger 136 attached to a plate 137 within the injection channel 134, where the injection channel 134 is defined by an injection cylinder 133 having an inner diameter sized substantially the same as an outer diameter of the seed 132 and an out diameter sized substantially the same as the loading port 112. With reference to dimensions discussed herein, substantially the same indicates that two measurements are the same or very close to one another, such as from 0.0-1.0 millimeters difference in diameter. For example, for a cylindrical seed 132 having an outer diameter of 0.8 mm, the injection channel 134 diameter (that is, the inner diameter of the injection cylinder 133) may be in the range of 0.8 mm-0.9 mm. This example seed diameter and example injection channel 134 diameter are considered substantially the same for purposes of this disclosure.

In operation, the plunger 136 is pressed towards the distal end 131 of the injector 130 in order to cause the plate 137 to move within the injection channel 134, thus forcing any object within the injection channel 134 out of the injection channel 134 at the distal end 131 of the injector 130. In some embodiments, the rod 135 of the plunger may include one or more supports that extend outward from and are sized to engage with the inner diameter of the injection channel. For example, the rod 135 may include multiple (e.g., 3-9) appendages extending outward along a length (or some portion of) the rod, such that the outer ends of the appendages engage with the inner diameter of the injection channel and support the rod 135 as it moves through the invention channel 134.

For purposes of clarity in the figures, reference numerals provided with reference to state A of FIG. 1 are not all included with reference to states B-F. In some embodiments, the plunger 136 may include a rod that is sized uniformly along a longitudinal length, without a separate larger plate 137. For example the rod may have a diameter that is substantially the inner diameter of the injection channel (e.g., the entire rod may be the size of the plate 137 in the example of FIG. 1). The embodiment of FIG. 14 uses such a plunger 1136, which may be used in other injector embodiments herein.

Moving to state B, the distal end 131 of the injector 130 has been placed into a loading port 112 of the loader 110. As noted above, in some embodiments the loading port 112 is sized to engage the outer diameter of the injection cylinder 133 of the injector 130. For example, the loading port 112 diameter may be from 0.0-1.0 millimeters larger than the outer diameter of the injection cylinder. Other embodiments of loading ports are discussed below with reference to other figures.

Next, at state C the plunger 136 has been moved towards the distal end 131 of the injector 130, which has correspondingly moved the seed 132 further towards the distal end 131 of the injector 130. Such movement may be performed by a human operator in a similar manner as a syringe may be used to administer an injection into a patient.

Continuing to state D, the plunger 136 has been further moved toward the distal end 131 such that the seed 132 has been injected into the desired position/portion of the carrier 120. With the seed 132 placed within the carrier 120, the injector 130 may be removed from the loader 110, such as is illustrated in state D of FIG. 1. In this example, removal of the injector 130 from the carrier 120 has created a void 122 in the carrier 120. Depending on the characteristics of the carrier 120, such as the material(s) of the carrier 120, the void 122 may be smaller or larger than is illustrated in FIG. 1. For example, with certain materials, such as collagen, the collagen that is displaced by insertion of the seed 132 may return to its original position such that the void 122 is insignificant. With other materials, however, a void may remain that is large enough to allow movement of the seed 132 within the carrier 120, such as when the carrier 120 is being moved and manipulated as it is moved into the treatment bed. Thus, in some embodiments, the seed 132 includes an adhesive on a distal end that enters the carrier 120 first, wherein the adhesive is configured to adhere to the carrier 120 and hold the seed 132 in place, even if a significant void 122 is created by the insertion process.

Furthermore, in some embodiments a plug 124 may be placed into the void 122 to contain the seed 132 at the desired location within the carrier 120. The plug 124 can be inserted in any manner, such as by manually pushing the plug 124 into the carrier through the loading port 112, possibly using a tool such as a screwdriver or chisel to ensure that the plug 124 is entirely in the carrier 120. Alternatively, the plug 124 can be placed using the injector 130 or a similar injection tool that allows placement of the plug in a similar manner as discussed above. In another embodiment, the seed and plug may be placed concurrently into the carrier 120 using an injector, such as by loading the injector with both the seed and plug, with the seed closest to the distal end 131 of the injector, and injecting both the seed 132 and plug 124 with the same movement of the plunger 136. The plug 124 can include an adhesive on one or more of its outer surfaces, such as a distal end and/or on the outer diameter, so that once inserted into the carrier 120 the adhesive adheres the plug to the carrier material. In other embodiments, the seed 132 may be further secured in place within the carrier 120 by suturing or otherwise closing the void 122.

In one embodiment, multiple seeds 132 may be inserted using a plunger similar to plunger 136, where the seeds may be separated by one or more spacers similar to plug 124. For example, the injection channel 134 may be loaded with a seed, then a spacer (e.g., a material similar to the plug 124, but sized to fit the spacing need(s)), then another seed. In this example, when the plunger is moved in order to evacuate the injection channel 134, the seed, spacer, seed series of objects are all injected into the carrier. Such combinations of multiple seed and spacer insertions may be used in any of the other embodiments discussed herein also, whether by manual or automatic process. Additionally, depending on the embodiment additional seeds and spacers may be inserted, such as a combinations of three seeds separated by two spacers, four seeds separated by three spacers, etc.

Figure 2:
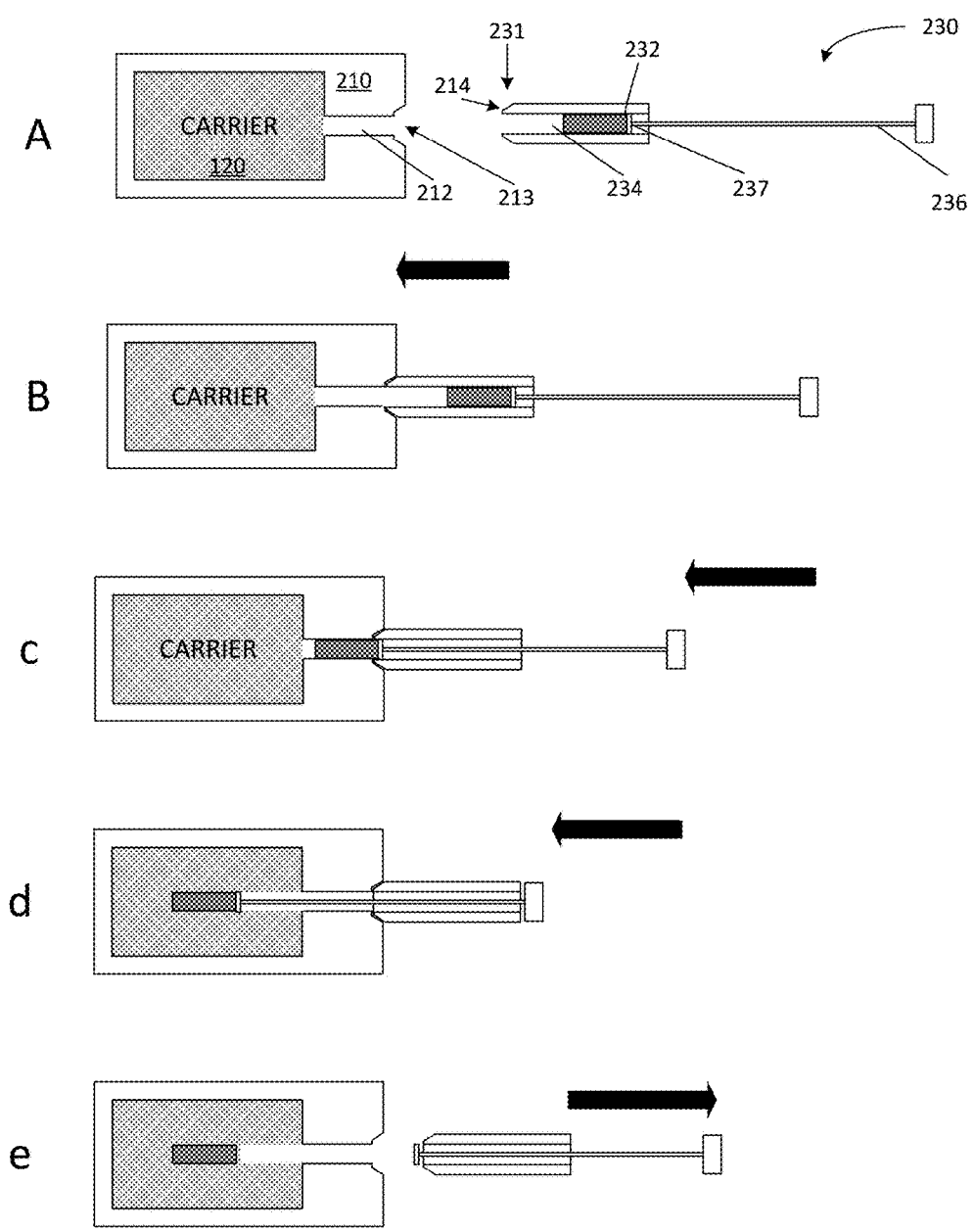
FIG. 2 is a cross-sectional view of another embodiment of a carrier that includes a port having an alignment interface configured to engage with a corresponding alignment interface at the distal end of the injector.

FIG. 2 is a cross-sectional view of another embodiment of a carrier 210 that includes a port 212 having an alignment interface 213 configured to engage with a corresponding alignment interface 214 at the distal end 231 of the injector 230. Similar to the injector 130, the injector 230 includes a plunger 236 connected to a plate 237 (or a plunger have a uniformly sized rod that without a separate plate 237, such as in the example rod 1336 of FIG. 14), which are configured to move a seed 232 through an injection channel 234 as the plunger 236 is urged towards the distal end 231 of the injector 230. However, the injector 230 additionally includes an alignment interface 214 on its distal end 231 that is the mirror of the alignment interface 213 of the loader 210. Thus, the injector 230 may be more securely interfaced with the loader 210 by means of the corresponding alignment interfaces of the loader 210 and the injector 230. The alignment interfaces 213 and 214 may advantageously allow more precise insertion of the seed 232 into the carrier 120 as an orientation of the injector 230 can be more precisely maintained as the alignment interface 214 is engaged with the alignment interface 213 of the loader 210

At state A of FIG. 2, the seed 232 has been loaded into the injector 230 and is ready for injection into the carrier 120. The seed 232 may be loaded in any manner, including the example loading methods discussed herein.

Moving to state B of FIG. 2, the injector 230 has been moved such that its alignment interface 214 is engaged with the alignment interface 213 of the loader 210. With the injector 230 engaged with the loader 210, at state C the plunger 236 may be urged towards the distal end 231 in order to push the seed 232 into the loader 210, and further into the carrier 120 as shown at state D. Finally, the injector 230 may be removed from engagement with the alignment interface 213 at state E. In some embodiments, an adhesive on the seed 232 and/or a plug may be used in order to more securely maintain the position of the seed 232 within the carrier 120, such as is discussed above with reference to FIG. 1.

Figure 3:
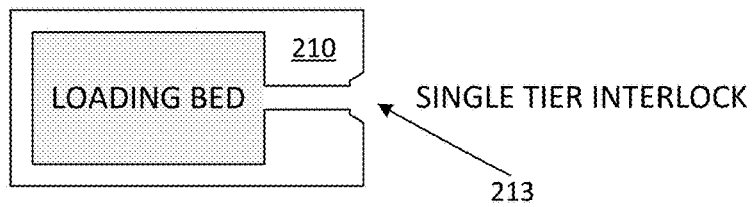
FIG. 3 is a cross-sectional view of several loaders, each with different alignment interfaces that are configured for engagement with a corresponding alignment interface of an injector.
Figure 3:
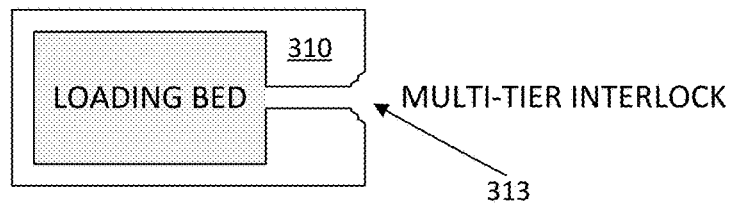
Figure 3:
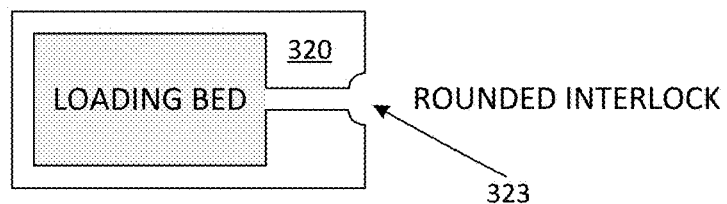
Figure 3:
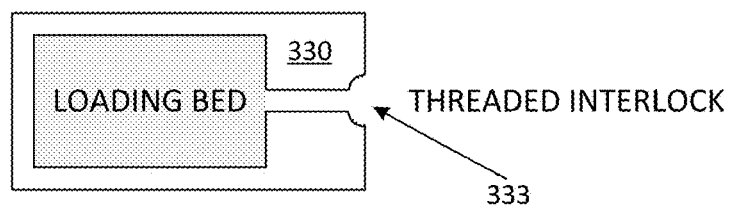
Figure 3:
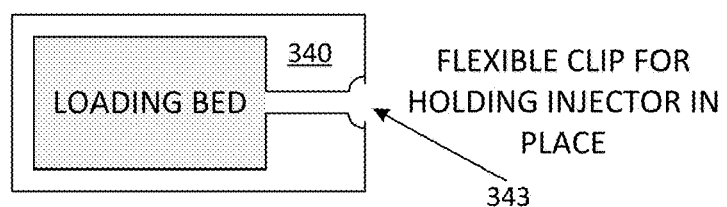

FIG. 3 is a cross-sectional view of several loaders, each with different alignment interfaces that are configured for engagement with a corresponding alignment interface of an injector. The loader 210 and its alignment interface 213, which were discussed with reference to FIG. 2, are illustrated in FIG. 3 for comparison with other possible alignment interfaces. Loader 310 includes a multi-tier interlocking alignment interface 313 and loader 320 includes a rounded interlocking alignment interface 323. Alignment interfaces 213, 313, 323 correspond to mirror-image alignment interfaces on distal ends of the injectors, such that the injector may be held in a specific position and orientation with reference to the respective loaders and carrier within the loaders.

Alignment interfaces 333 and 343 of loaders 330 and 340, respectively, may even more securely engage injectors with the loaders. For example, alignment interface 333 includes a female threaded portion configured to engage a male threaded alignment interface on the distal end of an injector. Thus, in this embodiment the injector can be threaded onto the loader 330 to be held in place more securely, such that movement of the injector while engaged with the loader 330 is less likely. Once the seed has been injected into the carrier, the injector can be unscrewed from engagement with the alignment interface 333. In the example of loader 340, the alignment interface 343 includes one or more flexible clips around the circumference of the entry to the injection channel of the loader 340. In this embodiment, the injector includes a corresponding one or more cavities at the distal end of the injector so that when the injector is engaged with the alignment interface 343, the clips of the alignment interface 343 are depressed until the corresponding cavities in the injector reach the clips (e.g., as the user pushes the injector into the loading port of the loader), whereupon the clips enter the cavities and hold the injector securely against the loader. As shown in the example loader 340, the alignment interface 343 may also include a shape similar to alignment interfaces 213, 313, 323, with the injectors having engagement interfaces that mirror the interfaces 213, 313, 323, in order to better hold the injector in place against the loader. In other embodiments any other configuration of alignment interfaces may be used in order to improve stability of engagement between an injector and loader as one or more seeds are injected into the loader.

Figure 4:
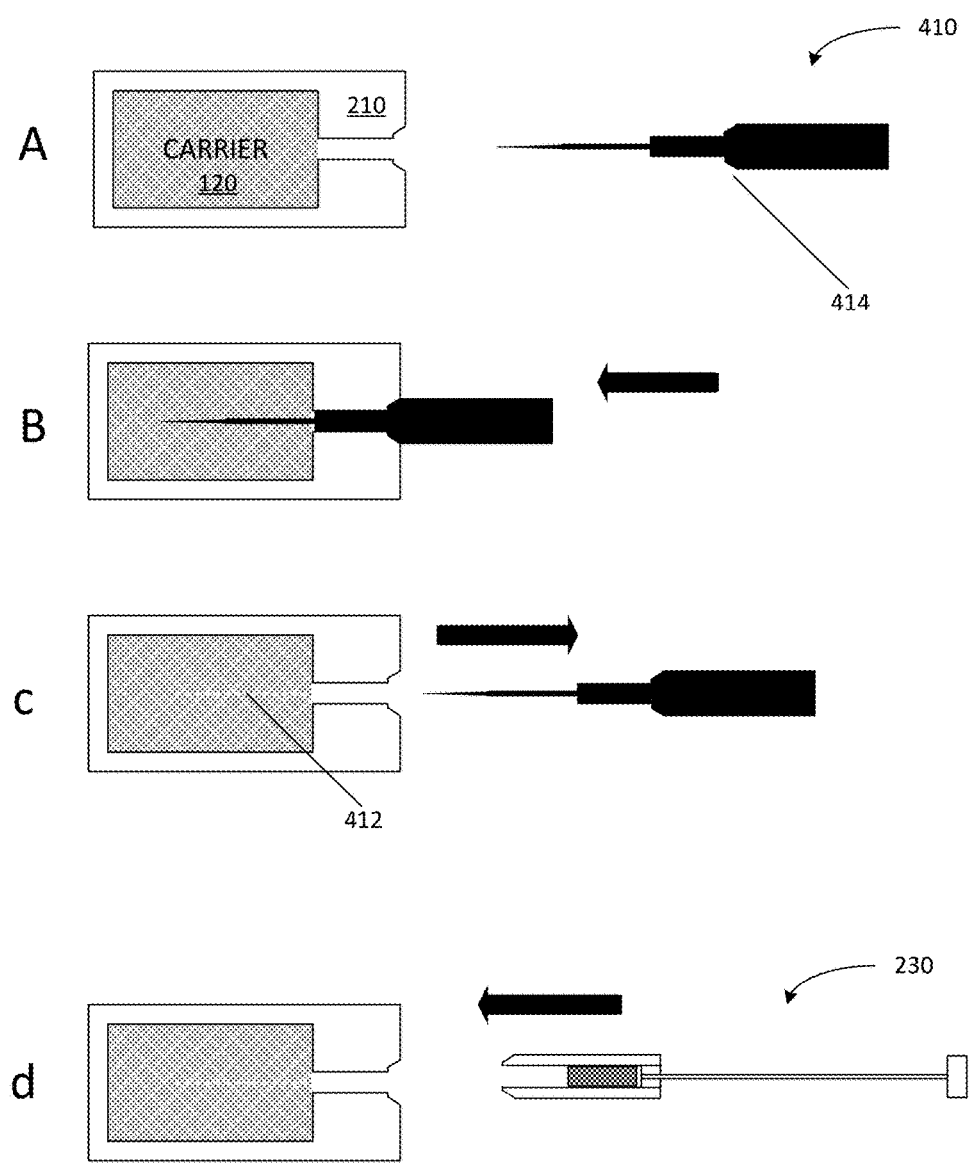
FIG. 4 is a cross-sectional view of an example carrier, a guide path tool, and injector.

FIG. 4 is a cross-sectional view of an example carrier 120, a guide path tool 410, and injector 230. The illustrated states of these components illustrates an example process of creating a guide channel 412 for insertion of a seed into the carrier 120, such as by using a guide path tool 410 that comprises a punch, lance, needle, trochar, blade, laser, chisel, screwdriver, drill, and/or other similar device. In the example of FIG. 4, a punch 410 (which may be replaced with any other similar device in other embodiments, such as those mentioned above) is used to create the guide channel 412 in the carrier 120 in order to decrease tension from a seed against the carrier material, which could result in disfiguring or crushing the seed and/or the carrier in some embodiments.

At state A in FIG. 4, the carrier 120 has been placed in the loader 210. While the punch 410 is illustrated in conjunction with the loader 210, the punch 410 and/or other similar guide channel creation instruments may be used in conjunction with any other loader, such as those illustrated in FIG. 3, whether in a manual loader or in an automated loader arrangement.

Moving to state B, the punch 410 has been inserted through the loading port of the loader 210 in order to create a guide channel 412 in the carrier 120, which can be seen in state C with the punch 410 now removed.

With a guide channel 412 in the carrier 120, a seed may more easily inserted into the carrier 120, such as using the injector 230 and the injection methods discussed above.

Figure 5A:
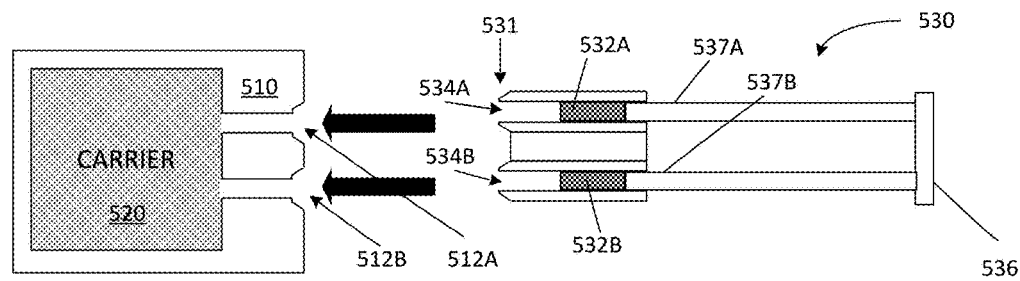
FIGS. 5A and 5B are cross-sectional views of example multi-port loaders and injectors.
Figure 5B:
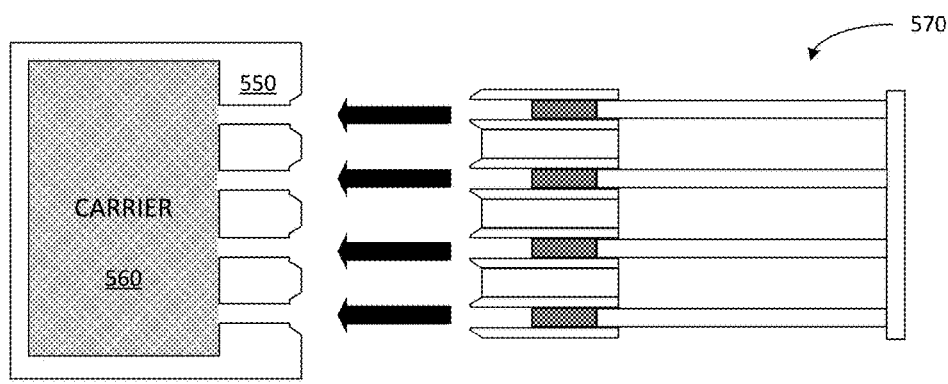

FIGS. 5A and 5B are cross-sectional views of example multi-port loaders and injectors. While these particular example loaders facilitate loading of two seeds and four seeds concurrently, respectively, carriers may include any other quantity of loading ports and injectors may include a corresponding quantity of injection channels holding seeds for injection into corresponding loading ports.

Beginning with FIG. 5A, the loader 510 includes two loading ports 512, including loading ports 512A and 512B. In this embodiment the loading ports 512 each include a single tier alignment interface, but in other embodiments different alignment interfaces may be used. The injector 530 includes two injection channels 534, including injection channel 534A and 534B. Each of these injection channels includes an alignment interface at the distal end 531 of the injector 530 that is configured to engage with the corresponding alignment interface 512 of loader 510. In this embodiment, the plunger 536 includes rods 537, including rods 537A and 537B, sized to substantially fill the injection channels such that movement of the plunger 536 towards the distal end 531 causes movement of both rods 537 within the corresponding injection channels 534 in order to urge the seeds 532 (e.g., seeds 532A and 532B) towards the distal end 531 and into the carrier 520.

As shown in FIG. 5A, the carrier 520 is a different size and shape than the carriers discussed in previous Figures. In this embodiment, the carrier 520 is configured to contain two seeds 532 (for example, seeds 532A and 532B). In other embodiments, other quantities of seeds may be inserted into the carrier 520 and/or other carriers. In some embodiments, carriers, such as carrier 520 and 560 (discussed below) are configured to be resized, such as in an operating room where the carriers are inserted into a tumor bed. Thus, certain carriers are configured for cutting, tearing, or breaking, in order to achieve a desired size and/or shape for appropriate insertion and therapeutic effect for the particular application of the carrier. In some embodiments, carriers include markings indicating to a user where it is safe to cut a carrier in order to avoid impacting an inserted radioactive seed. Thus, in embodiments where multiple seeds are injected into a carrier, markings may be included on the carrier that allow a user to cut the carrier into multiple single seed carriers for insertion into the tumor bed.

In FIG. 5B, the loader 550 includes four injection ports and the injector 570 includes four injection channels, each configured to contain one or more radioactive seeds. In this embodiment, the plunger of the injector 570 is coupled to injection plates within each of the four injection channels such that movement of the plunger towards a distal end of the injector 570 causes all four seeds to move towards the distal end and then into the carrier 560 (once the injector 570 has been engaged with the alignment interfaces of the loader 550).

Figure 6:
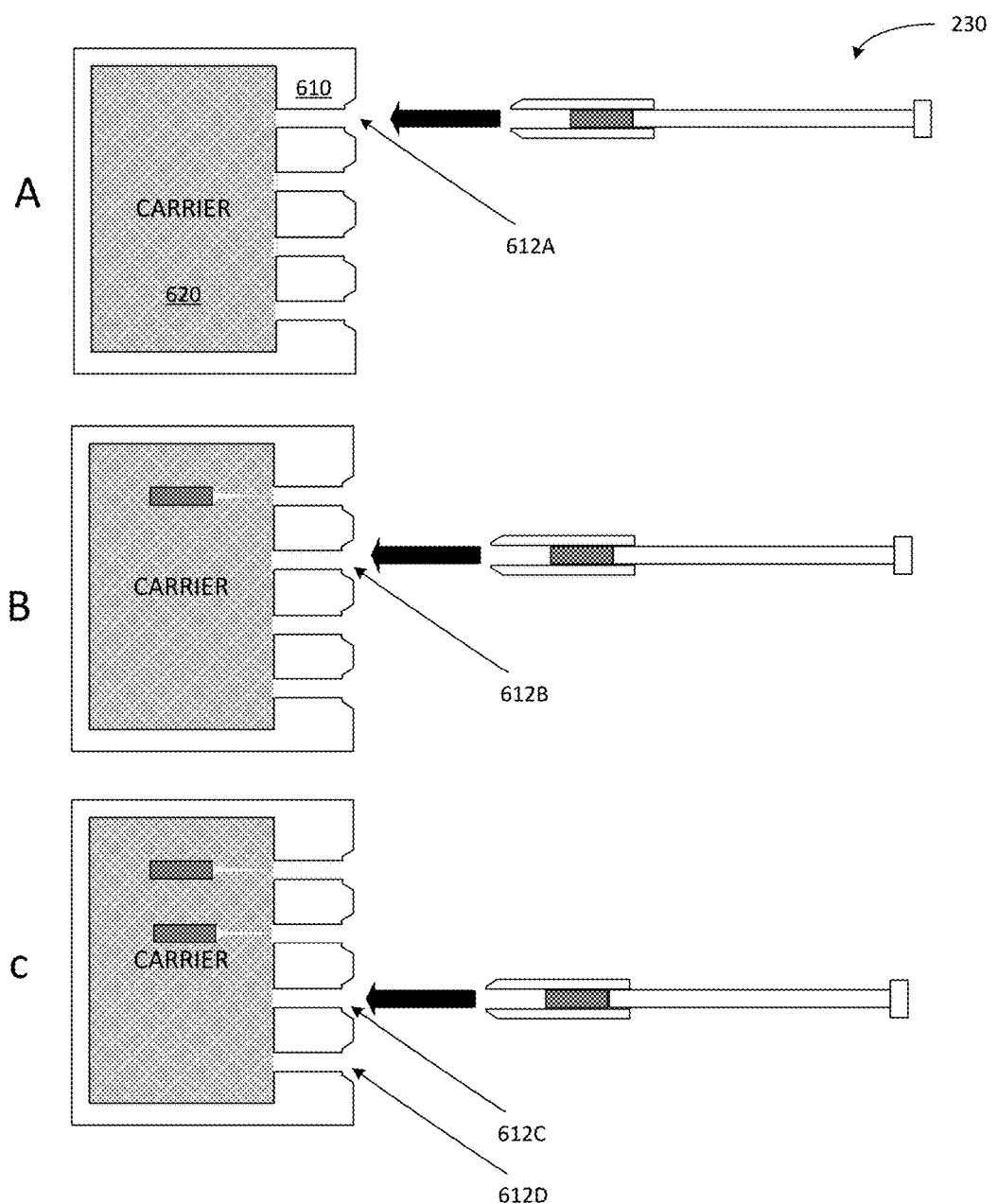
FIG. 6 is a cross-sectional view of a multi-port loader that is being loaded using a single channel injector (as discussed above with reference to FIG. 2, for example).

FIG. 6 is a cross-sectional view of a multi-port loader 610 that is being loaded using a single channel injector 230 (as discussed above with reference to FIG. 2, for example). At state A of FIG. 6, a carrier 620 has been placed in a loading bed of the loader 610, such as may be performed by a manufacturer of the loader 610 so that the carrier 620 is preloaded in the loading bed of the loader 610, or by the entity that injects the seeds into the carrier 620. The injector 230 is loaded with the seed and the seed is injected into a first port 612A of the loader 610 so that the seed is contained within the carrier 620, as shown in state B.

With the first seed in place within the carrier 620 (state B), the injector 230 can be reloaded with another seed and injected into a second loading port 612B of the loader 610. Similarly, with the second seed embedded in the carrier 620, as shown in state C, a third seed may be loaded in the same injector 230 and injected into the carrier via port 612C. While not shown, a fourth seed can also be loaded into the injector 230 and inserted into the carrier via port 612D. Such an iterative loading process can be performed with loaders having any number of loading ports and injectors having any number of injection channels and seeds. For example, a dual channel injector 530 (FIG. 5) may be used with the loader 610 to load two seeds into the carrier 620 concurrently, so that the process can be performed twice in order to load four seeds into the carrier.

Figure 7:
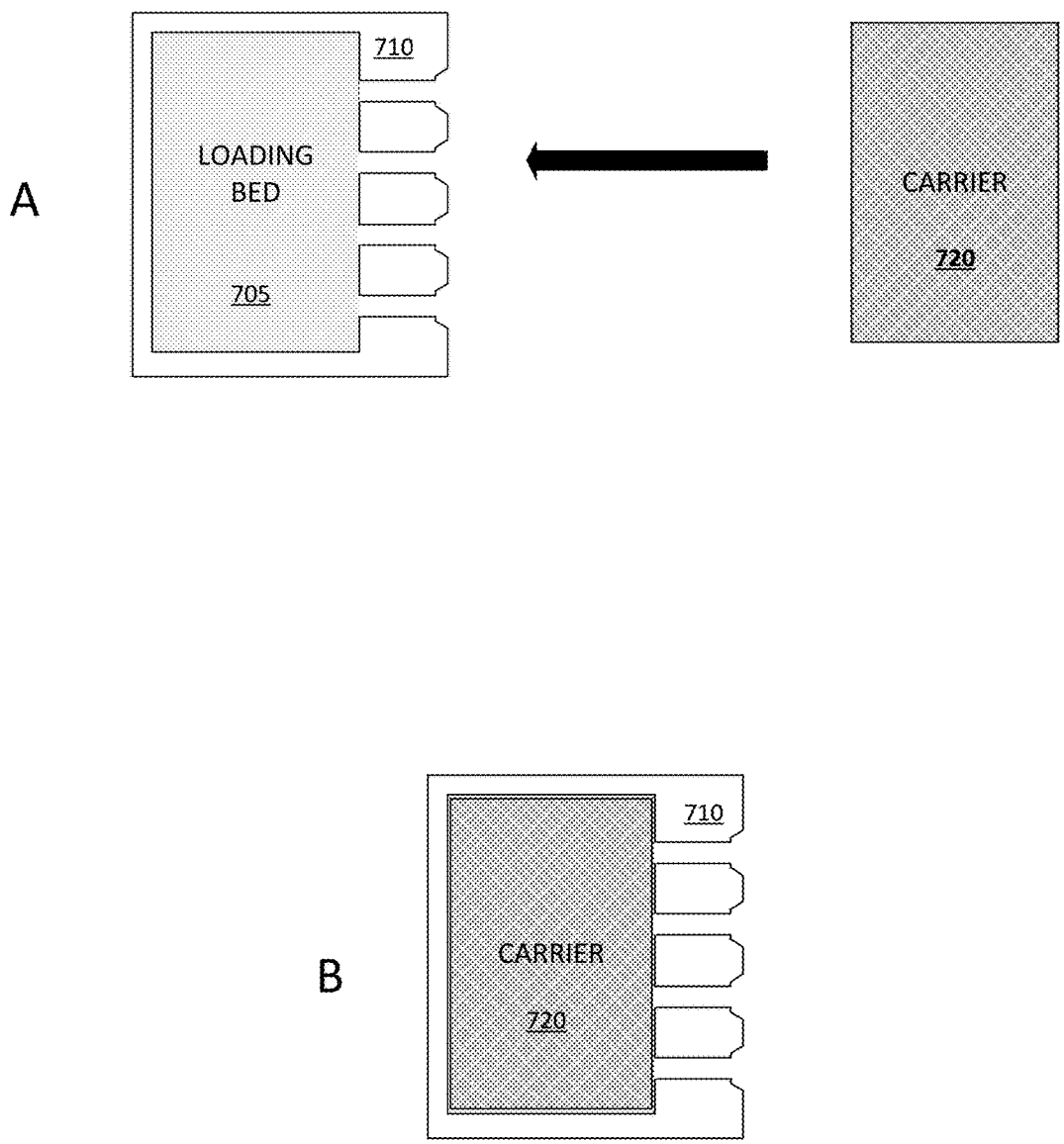
FIG. 7 is a cross-sectional view of a loader and a carrier during a process of loading the loader with the carrier.

FIG. 7 is a cross-sectional view of loader 710 and a carrier 720 during a process of loading the loader 710 with a carrier 720. In this example, the loader 710 is a four port loader, the loading bed 705 is rectangular, and the carrier 720 is similarly rectangular with a size substantially the same as the loading bed 705. However, in other embodiments the loading methods discussed herein may be used with any other loaders, loading beds, carriers, etc.

At state A, the loader 710 and carrier 720 are separate devices, which may be manufactured separately, purchased from separate entities, or manufactured and/or purchased from a single entity. The loading bed 705 is configured to engage with the carrier 720 in order to maintain a position of the carrier 720 within the loading bed 705. Various mechanisms may be used in the loading bed 705 in order to achieve stability of the carrier 720 therein. For example, the loading bed 705 may be sized to tightly fit the carrier 720 therein. In other embodiments, the loader 710 may include a lid that attaches to a top of the loader 710 and holds a top surface of the carrier 720 in place within the loading bed 705. In some embodiments the loader 710 includes a lid having a loading bed insert sized to fit within outer walls of the loading bed 705 and engage a top surface of the carrier 722 to more securely hold the carrier 720 in position within the loading bed 705. Various configurations and examples of loading beds are discussed in the co-owned patent noted above with reference to the definition of Loader. All such configurations and examples of loading beds and loader functionality is hereby incorporated by reference for all purposes.

Moving to state B, the carrier 720 has been placed into the loading bed 705. Depending on the embodiment, the carrier 720 may be manually placed into the loading bed 705. For example, a lid may be removed from a top of the loader 710 in order to expose the loading bed 705, the carrier 720 can then be manually placed into the loading bed, and then the lid can be replaced in order to further hold the carrier 720 within the loading bed 705 and/or to provide shielding against radiation from seeds once they are inserted into the carrier 720. In another embodiment, the loader 710 includes a slot through which the carrier 720 can be inserted, similar to how a VHS tape can be inserted into a VCR. In other embodiments, the carrier 720 can be loaded in any other manner. With the carrier 720 held in place within the loading bed 705, the carrier is now set to receive one or more seeds via an injector.

Figure 8:
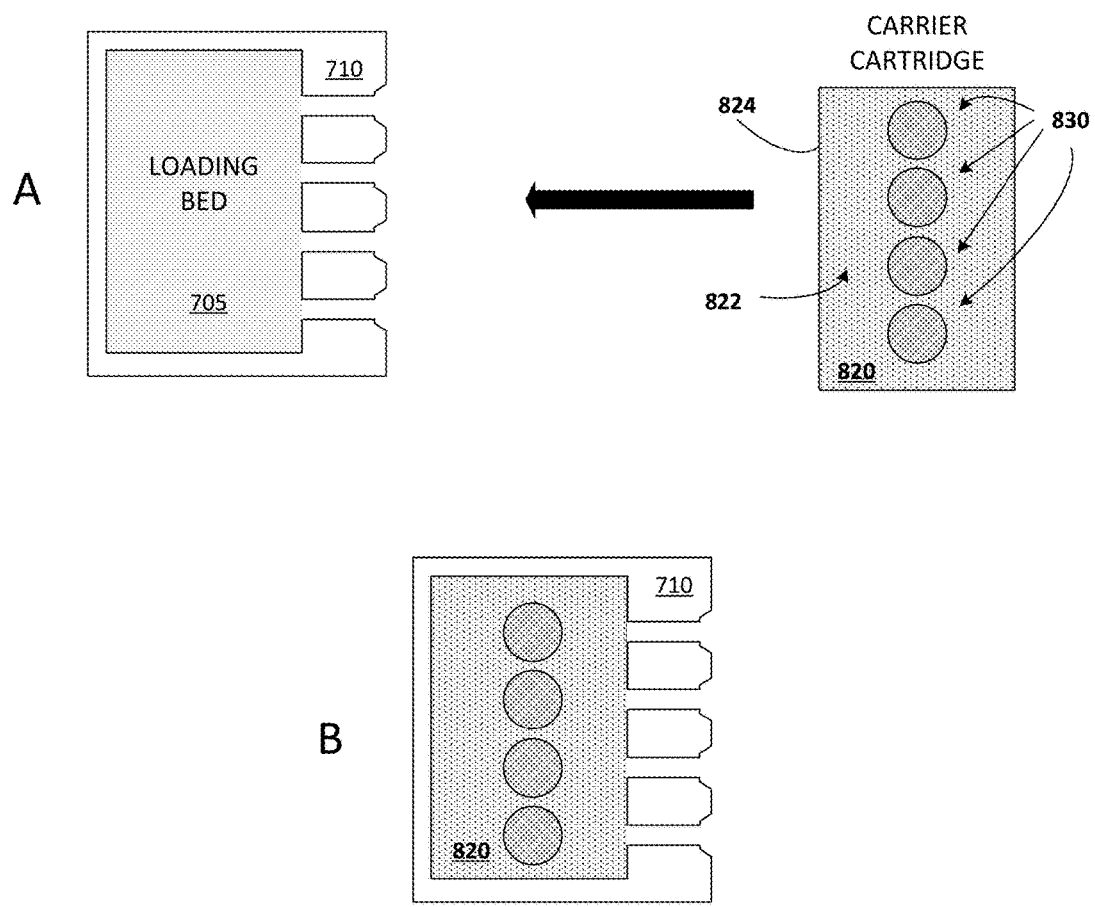
FIG. 8 is a cross-sectional view of the same loader, including loading bed, as illustrated in FIG. 7, but now the loading bed loaded with a carrier cartridge that holds multiple carriers in place.

FIG. 8 is a cross-sectional view of the same loader 710, including loading bed 705, as illustrated in FIG. 7, but now the loading bed 705 loaded with a carrier cartridge 820 that holds multiple carriers in place. The example carrier cartridge 820 comprises a hard outer shell 824 and a material 822 that is dense enough to hold the multiple circular carriers 830 in predetermined positions within the carrier cartridge 820. The shell 824 may be made of plastic, metal, or any other substance that maintains the shape of the carrier cartridge 820. The shell 824 and/or the carrier cartridge 820 may be formed of one or more of polyethylene, high density polyethylene, borated polyethylene, polyetherimide resin, polyurethane, polytetrafluorethylene, polyehtylene terephthalate, and/or any other suitable material.

In one embodiment, the shell 824 comprises a shielding material, such as a high z material, that provides radioactive shielding from seeds that are placed in carriers within the carrier cartridge 820. In some embodiments carrier cartridge 820 does not include a separate shell 824 material; rather, the outer surface of the carrier cartridge 820 is defined by the material 822. Thus, the carrier cartridge 820 may be molded (or formed by another manufacturing processing) in a single molding process.

In the example of FIG. 8, the circular carriers 830 are maintained in precise positions so that when the carrier cartridge 820 is loaded in the loading bed 705 and radioactive seeds are injected into the loader 710 via the multiple loading ports, the seeds are directed into a precise area of the respective carriers 830. For example, the carrier cartridge 820 may be configured to hold the carriers 830 such that the radioactive seeds are positioned in a center of the carriers 830. Depending on the embodiment, the carriers 830 may be positioned in various configurations within the carrier cartridge 820 in order to achieve various placements of seeds within the carriers. For example, some of the previous patents of the current assignee listed above with reference to the definition of Carrier include details regarding offset spacing of seeds within carriers, such as so a seed can be placed closer to a top surface of the carrier than to a bottom surface of the carrier (e.g., 1 mm from a top surface of a 4 mm thick carrier). In such an embodiment, the carrier can be placed in the tumor bed with the seed closer to the treatment area or, alternatively, that same carrier can be flipped over so that the seed is further from the treatment area if reduced radiation to the particular treatment area is desired. Placement, orientation, seed strength, and/or other characteristics related to a radiation therapy protocol may be determined manually or via one or more automated processes, such as the processes described in provisional application No. 62/113,252, filed Feb. 6, 2015, and titled "Implant Planning System And Implant Placement Guide System," which is hereby incorporated by reference in its entirety for all purposes.

At state B in FIG. 8, the carrier cartridge 820 has been loaded into the loader 710, and is ready for insertion of seeds into the carriers 830 using any suitable injector, such as those discussed above and/or any other injector.

Depending on the embodiment, the carrier cartridge 820 may be reusable or a single use cartridge. For example, a single use carrier cartridge may require removal of a portion of the carrier cartridge 802, such as by unsnapping, using break-away detents, or other mechanism by which the cartridge 820 is held together, such that the carriers 830 may be removed from the cartridge 820 after seed injection. In such an embodiment, the carriers 830 may be sterilely manufactured within the carrier cartridge 820 such that a user of the carriers 830 is not required to load the circular carriers 830 into the carrier cartridge 820. For example, a collagen manufacture that produces collagen carriers may place the carriers in a carrier cartridge 820 and seal the carrier cartridge 820 in a sterile environment for shipping to an end user. In other embodiments, the carrier cartridge 820 includes wells or slots wherein carriers can be interchangeably placed therein, loaded with seeds, and removed. In such an embodiment, the carrier cartridge 820 may be reused indefinitely. Such a carrier cartridge is discussed below with reference to FIG. 10.

In some embodiments, a carrier cartridge may include a gridded pattern or other feature to allow a radiograph to be taken after seed loading, so seed positions can be confirmed. In some embodiments, a punch is used to create a guide channel through the shell 824 of the carrier cartridge 820, the carrier material 822, and/or the carrier 830 itself in order to allow easier insertion of the seed from outside the carrier cartridge 820 into the carrier. For example, a single punch tool may be configured to penetrate each of these materials to create a guide channel for seed placement.

Figure 9:
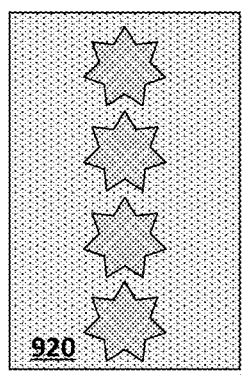
FIG. 9 illustrates three additional example carrier cartridges containing carriers of varying shapes.
Figure 9:
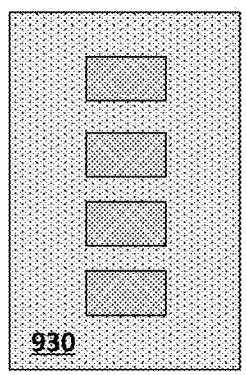
Figure 9:
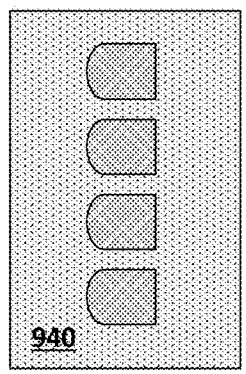

FIG. 9 illustrates three additional example carrier cartridges 920, 930, and 940. As with carrier cartridge 820, each of these carrier cartridges may be preloaded with carriers, or may include wells, slots, or other openings where carriers can be loaded into the cartridge. As shown in FIG. 9, the carrier cartridge 920 is loaded with four star shaped carriers, the carrier cartridge 930 is loaded with four rectangular shaped carriers, and the carrier cartridge 940 is loaded with four Gore shaped carriers.

Figure 10:
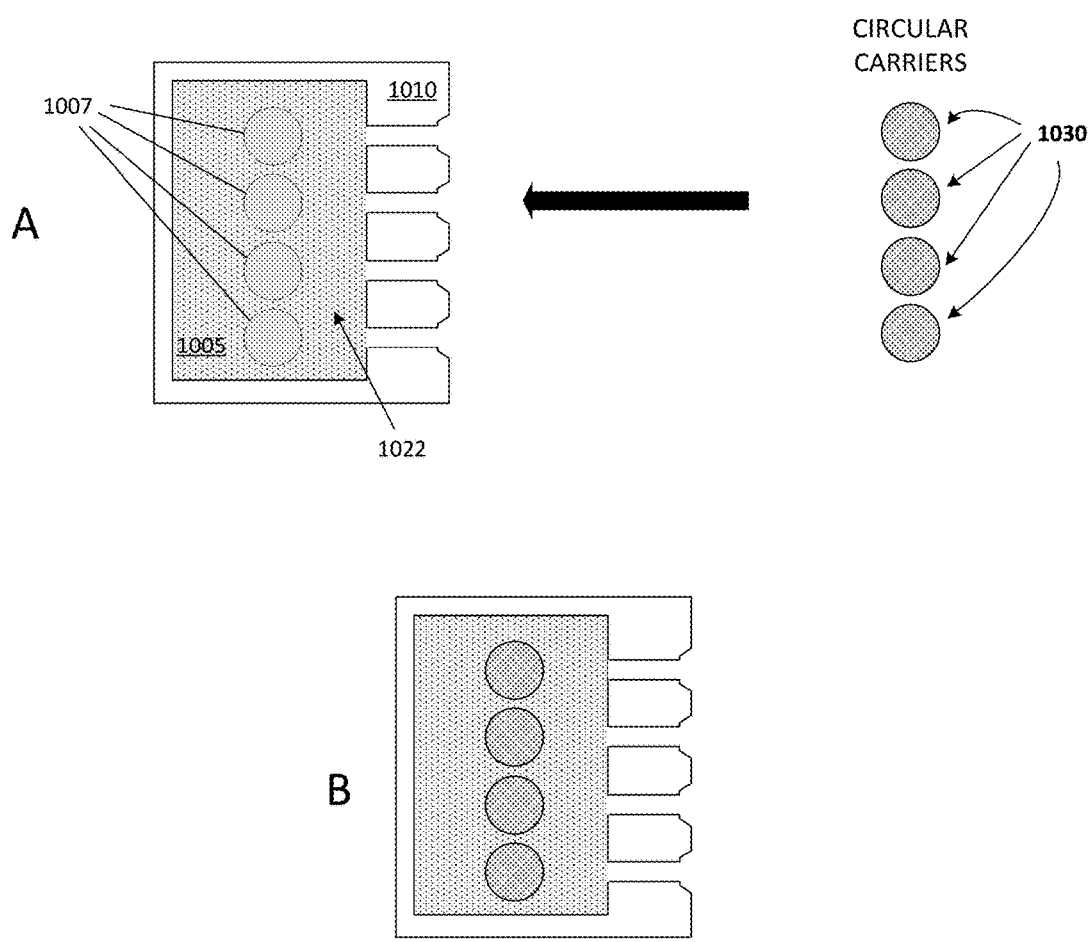
FIG. 10 is a cross-sectional view of a loader having a loading bed that includes wells sized to receive circular carriers.

FIG. 10 is a cross-sectional view of a loader 1010 having a loading bed that includes wells 1007 sized to receive circular carriers 1030. In this embodiment, the wells 1007 may be integrally formed as part of the loader 1010, such that the wells 1007 are positioned at precise locations to maintain carriers at the desired location for seed injection. In another embodiment, the wells are part of a carrier cartridge that is pre-inserted into the loader 1010 prior to insertion of carriers into the wells of the carrier cartridge. For example, the carrier cartridge may be an integral part of a loader. In one embodiment, the carrier cartridge includes a channel from each of the injection ports to the wells 1007 sized and configured to allow a seed to be injected through the carrier material 1022. In other embodiments, a punch may be used to create guide channels through the carrier material, and into the carriers in some embodiments. In other embodiments, the carrier material 1022 is configured to allow a seed to move through the carrier material 1022 into the carrier without a pre-created channel.

As shown at state B in FIG. 10, each of the carriers 1030 has been inserted into a corresponding well 1007 of the loader 1010. The carriers 1030 may be inserted manually, such as by a user's hands, tweezers, pliers, etc. placing each of the circular carriers into wells one at a time, or the process may be automated by a device that places the circular carriers 1030 into the wells 1007.

Figure 11:
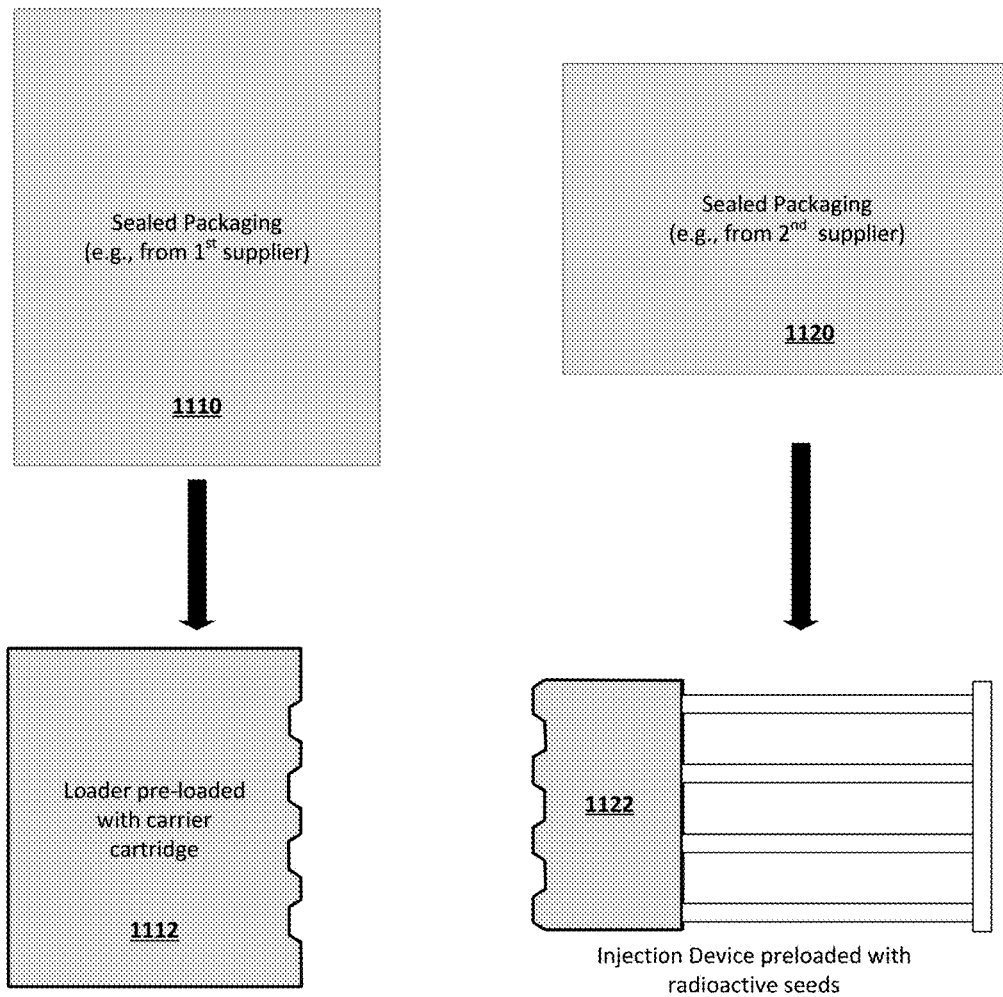
FIG. 11 illustrates an example use case of the loader and injector systems discussed herein.
Figure 11:
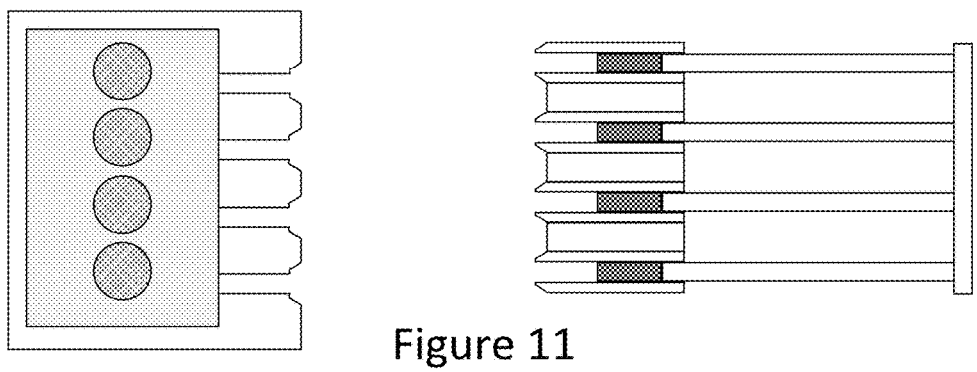

FIG. 11 illustrates an example use case of the loader and injector systems discussed herein. In the example of FIG. 11, exposure to radiation by one or more individuals that load the carrier(s) with radioactive seeds is reduced by pre-packaging of components used in the process by suppliers of the loader and/or the injector. Thus, rather than pre-inserting seeds into carriers (e.g., creating hot carriers) before they are inserted into a body (e.g., creating hot carriers by a manufacture prior to shipping), it may be advantageous to provide components that allow easy injection of seeds into carriers just prior to the expected implantation of the carriers, while also reducing risk of excessive radiation exposure to the user that loads the carriers.

Separation of the carriers from seeds until time of application may provide one or more advantages. For example, the usable life of a carrier (e.g., collagen) compared to seeds may be vastly different. Seeds are typically configured for use (e.g., insertion into a tumor bed for delivery of radiation) within 5-10 days (or less) from manufacture. Collagen, however, may be useful for two years or more without appreciable deterioration in properties. Because both seeds and carriers are expensive, once they are combined into a hot carrier, the effective life of the hot carrier begins to elapse and if not used within the determined useful time frame of the seed, the combination of both seed and carrier becomes useless. Thus, use of the loading systems and methods discussed herein provide a "just in time" solution for combining seeds with carriers to minimize waste of pre-loaded hot carriers. Loading of seeds using the systems and methods discussed herein may take place at various locations and may be performed by various personnel. For example, loading can take place at the location where seeds are made (e.g., "hot carriers" may be made to order for a particular patient and dosimetry plan), with pre-packaged collagen (again, long shelf life) being combined with seeds, and shipped (e.g., overnight by a common carrier, such as FedEx) to point of use (e.g., an operating room). Alternatively, a variety of "cold" carriers and/or carrier cartridges could be stocked at the hospital, like any other sterile semi-durable supply (e.g., such as I.V. catheters). Seeds may then be pre-ordered and accessible to the operating room. For example, an expected supply of seeds (e.g., of varying radioactivity levels, sizes, shapes, etc.) may be kept on hand at the hospital and usable on demand. Thus, when an operation takes place and a tumor bed is assessed, a dosimetry may be planned (and/or confirmed from prior planning) and seeds loaded into one or more carriers (e.g., tiles, gores, stars, or a combination as suits the need). In this implementation, if not used within the usable lifetime, seeds may be wasted components, but collagen typically will not be wasted because of its longer useful lifespan.

In FIG. 11, a sealed packaging 1110, such as from a first supplier, may be purchased and received by an end user, such as a surgeon that is implementing a radiation treatment plan after a tumor removal surgery has been performed on a patient. In this example, the sealed packaging includes a loader 1112 that is preloaded with a carrier cartridge having one or more carriers therein. Thus, the surgeon (or other user) is not required to load carriers into the loader. In some embodiments, the loader may be preloaded with a single carrier, or the loader may be shipped along with a carrier cartridge preloaded with carriers that can be placed in the loading bed of the loader 1112 by the end user.

In this example, sealed packaging 1120 contains an injection device 1122 that is preloaded with radioactive seeds configured for injection into the carriers within the loader 1112. In this example, the loader 1112 includes four loading ports and the injection device 1122 includes four injection channels that are visible in the cross section views at the bottom of FIG. 11. As discussed above, the injector 1122 may be engaged with the loader 1112 via the alignment interfaces on each device, and the seeds may be injected into the carriers by pressing the plunger towards the loader 1112 in order to inject multiple (four in this example) seeds into the carriers concurrently. Once the carriers become "hot", having seeds loaded therein, the carriers may be removed from the loader 1112 in various manners, such as by removing a lid (not shown; see related "loader" patent noted in definition section for examples of lids) of the loader 1112.

Figure 12:
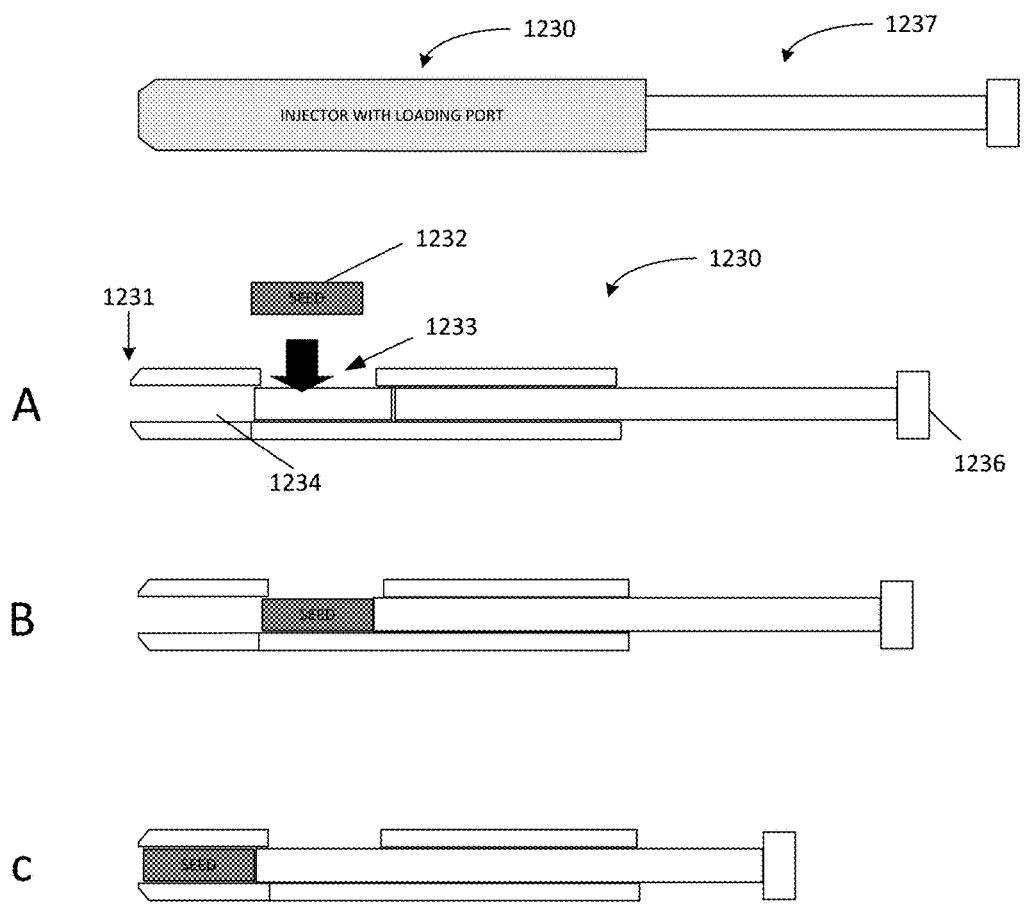
FIG. 12 illustrates an injector that includes a loading port for loading seeds into the injection channel.

FIG. 12 illustrates an injector 1230 that includes a loading port for loading seeds into the injection channel. As discussed in some of the embodiments above, the seed may be placed in the injection channel at the distal end of the injector. In other embodiments, seeds may be loaded in other manners, such as those discussed below.

The top illustration of injector 1230 is an example external view of the injector 1230, while the remaining three illustrations are cross-sections of the same injector 1230 that illustrate operation of the injector 1230. In particular, at state A the injector 1230 has not yet been loaded with the seed 1232. The injector 1230 includes components similar to those discussed in various other embodiments, including an injection channel 1234, a plunger 1236 (having a uniformly sized rod 1237 in this example, but could include a smaller rod and a plate in other embodiments), and a distal end 1231 that includes an alignment interface configured to engage with a similar alignment interface on a loader. In this embodiment, however, the injector 1230 includes a loading port 1233, such as an opening in the injection cylinder sized to allow a seed 1232 to pass from outside the injector 1230 into the injection channel 1234. In one embodiment, the loading port 1233 is sized horizontally and/or vertically to the precise dimensions of the seed intended for use in that particular injector 1230, such that, for example, seeds that are too big for the injector may not be inserted (and potentially jam the injector) and seeds that are too small may be identified prior to or as they are placed into the loading port 1233 in response to a user identifying that the seed does not fit tightly within the size constraints of the loading port 1233.

At state B, the seed 1232 has been moved through the loading port 1233 and is in the injection channel 1234. With the seed in the injection channel 1234, the plunger 1236 may be moved towards the distal end 1231 in order to urge the seed 1232 out of the injection channel 1234 into a carrier.

Figure 13:
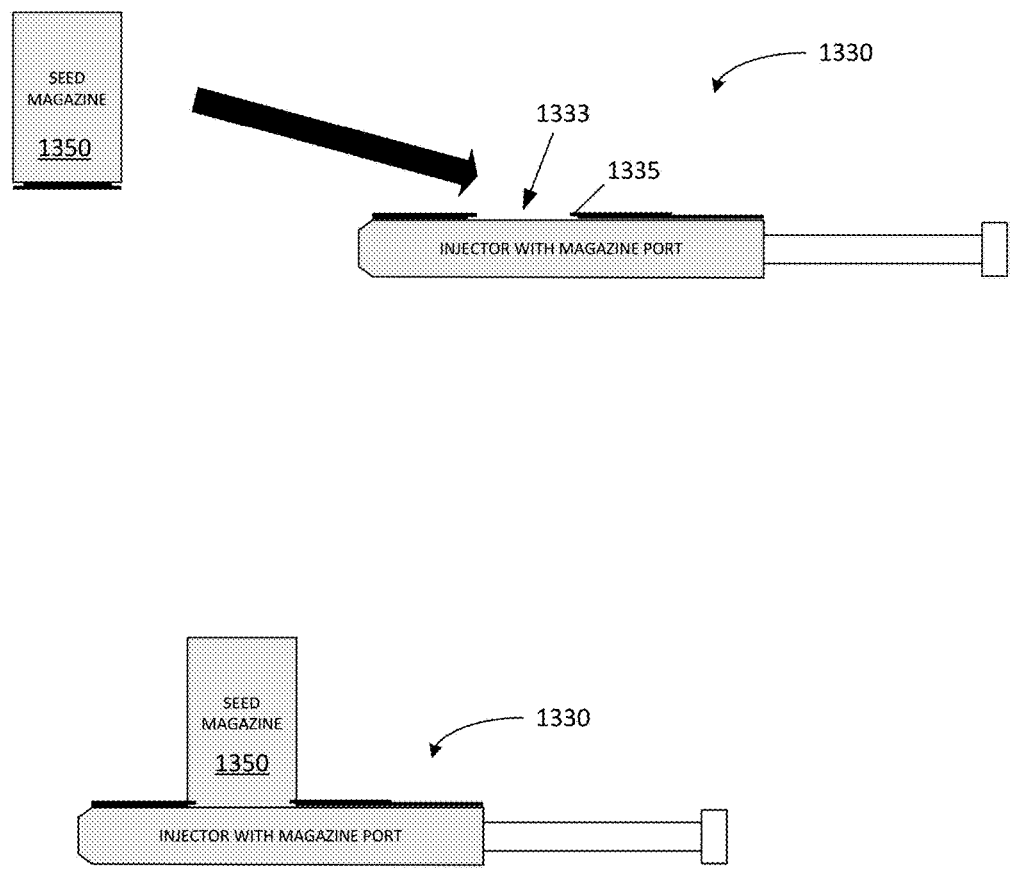
FIG. 13 is a diagram illustrating an example external view of an injector with a magazine port, and a seed magazine configured for attachment to the injector via the magazine port.

FIG. 13 is a diagram illustrating an example external view of an injector with a magazine port, and a seed magazine configured for attachment to the injector via the magazine port. In this embodiment, the injector 1330 includes a magazine port 1335 that fixedly receives the seed magazine 1350 so that the seed magazine 1350 can access the injection channel of the injector 1330 via the loading port 1333. As shown in the lower illustration in FIG. 13, the seed magazine 1350 has been fixedly attached to the injector 1330 and, in this configuration, the injector 1330 may be used to inject multiple seeds (e.g. a quantity defined by how many seeds are in the seed magazine 1350) without manual loading of each seed into the injector 1330 separately.

In this embodiment, the magazine port 1335 comprises a locking mechanism, such as a mechanism that might be found on a gun for receiving and attaching an ammunition clip thereto, which secures the seed magazine 1350 onto the injector 1330 while the injector 1330 is in use. Once the seeds from the seed magazine 1350 have all been injected into carriers by the injector 1330, the seed magazine 1350 may be removed and replaced with another seed magazine having seeds loaded therein. In some embodiments, the seed magazine 1350 is reloadable, such that an empty seed magazine 1350 may be loaded by a technician, or an automated machine, by pushing seeds into the seed magazine 1350. This reloading process may be similar to the process of loading an ammunition clip with rounds of ammunition.

Figure 14:
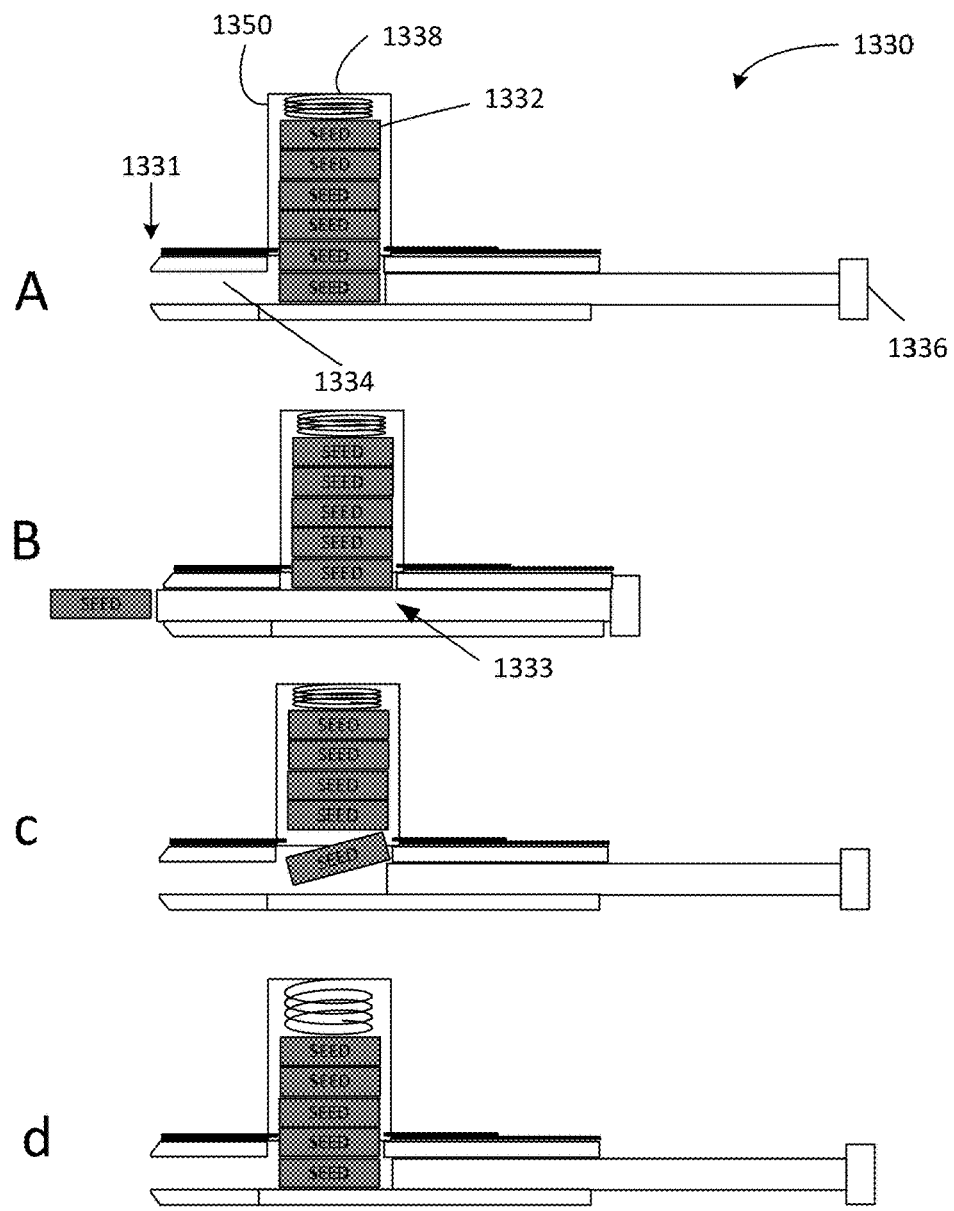
FIG. 14 illustrates a cross-sectional view of an injector in various states as a seed magazine is used to move seeds into the injection channel one at a time for injection into a carrier.

FIG. 14 illustrates a cross-sectional view of injector 1330 in various states as a seed magazine 1350 is used to move seeds 1332 into the injection channel 1334 one at a time for injection into a carrier. As shown at state A, the seed magazine 1350 includes a force providing source, such as a spring 1338, that pushes seeds downward towards the loading port 1333 of the injector 1330, and then into the injection channel 1334. While a spring 1330 is shown in FIG. 14, any other component that provides a force against the seeds towards the loading port 1333 may be used.

Moving to state B, the plunger 1336 has been moved towards the distal end 1331 in order to move the seed out of the injection channel 1334 (and into a carrier preferably). At state C, the plunger 1336 is then moved away from the distal end 1331 and as it moves past the loading port 1333, the force applied by the spring 1338 causes a next seed to enter the injection channel 1334 via the loading port 1333. Thus, at state D the next seed is in the injection channel 1334, ready for implantation into a carrier by movement of the plunger 1336 towards the distal end 1331. This process (e.g. moving the plunger forward to inject seeds into carriers and then pulling the plunger back to allow a next seed to be forced into the injection channel by the spring 1338) may be repeated until all of the seeds in the seed magazine 1350 have been injected or the desired number of seeds is used, even if seeds remain in the magazine. As noted above, the seed magazine 1350 may be replaceable, such that it can be removed and replaced with another seed magazine 1350 in order to inject additional seeds using the same plunger 1336. In other embodiments, the seed magazine 1350 is integrally attached to the plunger 1336, such that when the seeds are all injected, the seed magazine 1350 cannot be refilled. Such a one-time use (where one-time use includes injection of multiple seeds that are in the seed magazine 1350) may advantageously limit exposure to radiation by a user that could otherwise be absorbed when the seed magazine 1350 is handled, attached to the injector 1330, and/or removed from the injector 1330.

In other embodiments, other mechanisms for loading multiple seeds into a single injection channel, such as one after another as they are inserted into different carriers or areas of a carrier, may be used. For example, a rotating multi-chamber loader, such as a revolving chamber of a revolver gun or a multi-color ball point pen, may be attached to the injector and rotated to alternate the position of the rotating loader in order to select chambers of the loader to align with the injection channel. In this way, such a rotating multi-chamber loader may be loaded (e.g., pre-loaded by a manufacturer and/or loaded by a user performing the seed injection) with multiple seeds (e.g., one seed per chamber of a multi-chamber loader, such as a loader having 3, 4, 5, 6, 7, 8, 9, 10, or any other number of rotatable loading chambers) so that the injections can be "re-loaded" with another seed simply by rotating the multi-chamber loader.

Figure 15A:
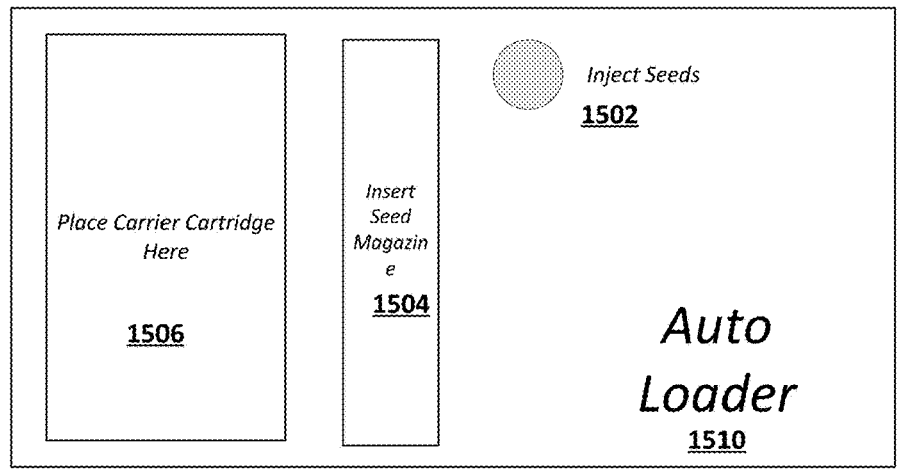
FIG. 15A illustrates an example "auto loader" that automates much of the process of loading seeds into carriers.

FIG. 15A illustrates an example "auto loader" that automates much of the process of loading seeds into carriers. In this example, the auto loader 1510 includes a carrier cartridge port 1506, a seed magazine port 1504, and an injection button 1502. In operation, a user can place a carrier cartridge into the port 1506, a seed magazine into the port 1504, and then simply press the injection button 1502 in order for the auto loader 1510 to inject the seeds into the carriers within the carrier cartridge, without further human involvement. The user can then remove the carrier cartridge from the port 1506 and access the hot carriers (loaded with radioactive seeds) for use in radiotherapy treatment of a patient, for example.

Depending on the embodiment, the auto loader 1510 may perform the seed insertion in many manners. In one embodiment, the auto loader 1510 comprises electromechanical parts, such as one or more servomotors that are arranged to extend in a similar manner as the plungers discussed with reference to other embodiments above in order to push seeds contained in the seed magazine into carriers within the carrier cartridge. Depending on the embodiment, the seed magazine may take on different forms. In one embodiment the seed magazine comprises a series of seeds each having access to an exit port (e.g., such as by breaking a perforation that holds the seeds in the magazine prior to insertion into the auto loader 1510, but that is easily broken when the seeds are pressed outward) that are aligned with the ports of the carrier cartridge such that seeds can be pressed directly out of the seed magazine into the appropriate ports of the carrier cartridge and further into the appropriate locations within the carriers. Thus, in one embodiment the carrier cartridge and seed magazine are paired, such that the positions of carriers within the carrier cartridge matches the spacing of seeds within the seed magazine.

Figure 15B:
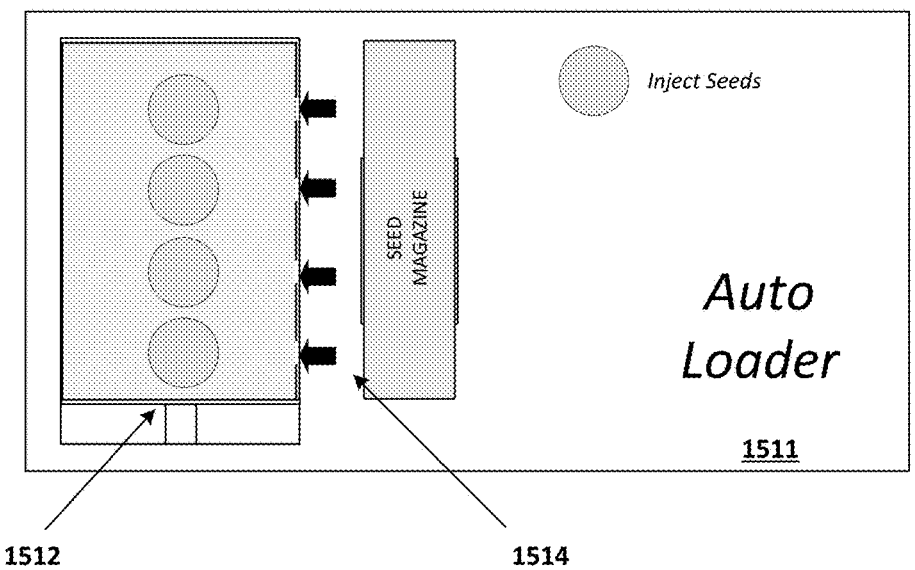
FIG. 15B illustrates another example autoloader, including a cross-sectional view of the loader.

FIG. 15B illustrates another example autoloader 1511, including a cross-sectional view of the loading bed. In this embodiment, the loading bed that receives the carrier cartridge is adjustable, such that different sizes, shapes, and/or orientations of carrier cartridges and/or carriers can be held securely in the loading bed. In the example illustrated, an adjustable member 1512 is included in the loading bed such that the user can slide the member back and forth within the loading bed in order to decrease an effective size of the loading bed and more tightly contain a smaller carrier cartridge and/or carrier. In other embodiments, a similar adjustable member may be included on the orthogonal dimension, such that the carrier cartridge may be tightly contained on all sides.

In this embodiment, the auto loader 1511 includes four sliders 1514 that are movable by a user to indicate positions of carriers within the loading bed and/or positions in which seeds should be inserted into the carrier(s) within the loading bed. In one embodiment, for example, the sliders are attached to respective loading channels that extends between the seed magazine and the loading bed, such that movement of the sliders adjusts a loading channel through which seeds are pushed when the injection button is pressed and the electromechanical components within the auto loader 1511 are activated. In this way, custom seed loading patterns could be generated within a single carrier, such as seeds that are placed asymmetrically within a carrier. Additionally, each of the loading channels may be set to deliver different seeds (e.g., different radioactivity, sizes, etc.) and/or different quantities of seeds to a particular carrier. For example, the auto loader 1511 may be set to deliver three seeds in a first channel, two seeds in a second channel, one seed in a third channel, and no seeds in a fourth channel.

Figure 16:
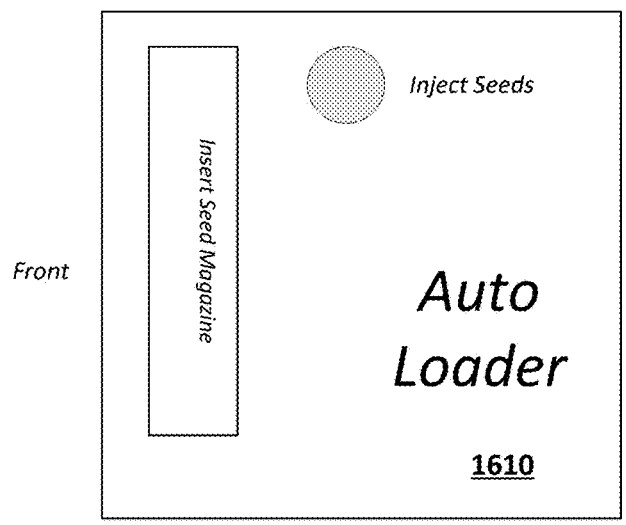
FIG. 16 illustrates a top and a front view of an auto loader.
Figure 16:
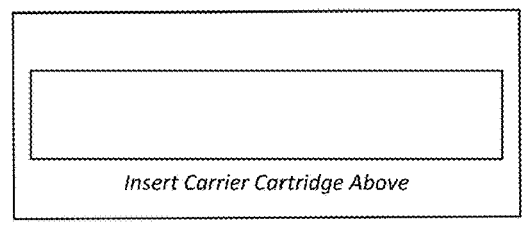

FIG. 16 illustrates a top and a front view of an auto loader 1610. In this embodiment, a seed magazine is inserted on a top of the auto loader 1610, and the carrier cartridge is inserted on the front of the auto loader 1610. In this embodiment, the carrier cartridge and seed magazine may engage one another when fully inserted, as each is supported by a separate portion of the auto loader 1610 frame. Thus, alignment of seeds within the magazine and loading ports within the carrier cartridge may be more precise.

Figure 17:
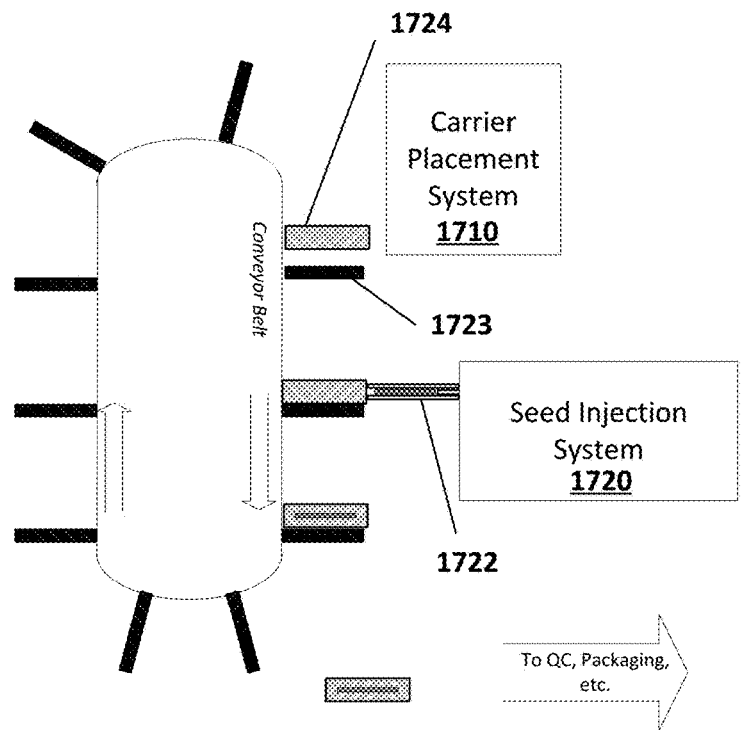
FIG. 17 illustrates example components that are usable in an automated process of loading seeds into carriers.

FIG. 17 illustrates example components that are usable in an automated process of loading seeds into carriers. In this particular example, a carrier placement system 1710 includes one or more electronic and/or mechanical components that deliver carriers to a conveyor belt, such as the vertically oriented conveyor belt system illustrated in FIG. 17. In this example, the conveyor belt includes multiple supports 1723 that are each sized to support a carrier 1724 as it is received from the carrier placement system 1710. In this example, the conveyor belt moves in a clockwise direction, such that the carriers 1724 are placed on supports 1723 near a top of the system and then are moved down as the conveyor belt and supports 1723 are moved downward. In other embodiments, configurations of automated systems for delivery of carriers may be performed by any known or later developed robotics and/or manufacturing processes. In this example, the conveyor belt moves the carriers 1724 downward towards a seed injection system 1720 that includes electromechanical components configured to operate a seed injector 1722 in order to inject a seed (or multiple seeds in some embodiments) into each of the carriers 1724.

In the example illustrated, the seed injector 1722 operates in a similar manner as the injectors discussed above, such as by a plunger being moved through an injection channel in order to force a seed out of the injector 1722 and into an adjacent carrier 1724.

In one embodiment, the conveyor belt stops momentarily when a carrier is positioned to be loaded with the seed. This pausing may be performed based on an expected uniform spacing of supports 1723 on the conveyor belt or may be performed in response to optical and/or mechanical components sensing that a carrier is in the appropriate position for seed injection.

In the embodiment illustrated, the seed injector 1722 may be reloaded with seeds using automated loading components such as those discussed above with reference to FIG. 14, for example.

Figure 18:
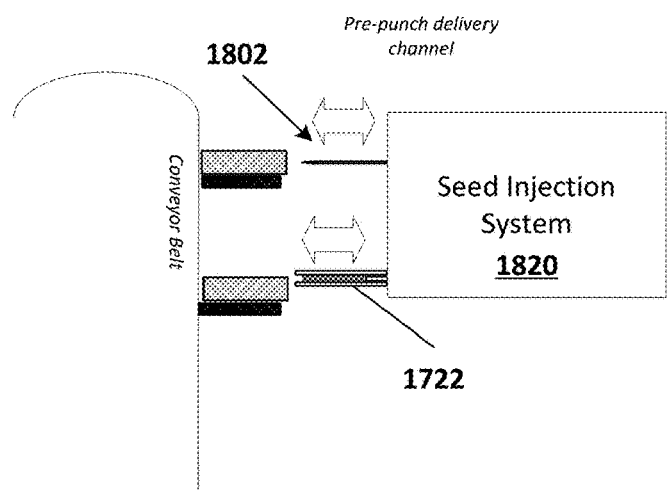
FIG. 18 illustrates another seed injection system that may be used in place of the seed injection system of FIG. 17 and/or in any other automated seed injection embodiment.

FIG. 18 illustrates another seed injection system 1820 that may be used in place of the seed injection system 1720 of FIG. 17 and/or in any other automated seed injection embodiment. In this example, the seed injection system 1820 includes the same or similar seed injector 1722, but also includes a guide path creation tool 1802 that is configured to move left to right (in this particular implementation) in order to puncture each carrier at a precise location where the seed injector 1722 will later insert the seed into the carrier. The guide path creation tool 1802 creates a guide path that allows the seed to more easily be inserted into the carrier material. With use of a guide path creation tool 1802, rectangular shaped seeds may be more reliably inserted into carriers using this automated process, minimizing damage to the seed and carrier material. In other embodiments, the carriers may have a guide path pre-punched such that the seed injection system does not need to create the guide path.

Other Embodiments

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

It should be emphasized that many variations and modifications may be made to the above-described embodiments, the elements of which are to be understood as being among other acceptable examples. All such modifications and variations are intended to be included herein within the scope of this disclosure. The foregoing description details certain embodiments of the invention. It will be appreciated, however, that no matter how detailed the foregoing appears in text, the invention can be practiced in many ways. As is also stated above, the use of particular terminology when describing certain features or aspects of the invention should not be taken to imply that the terminology is being redefined herein to be restricted to including any specific characteristics of the features or aspects of the invention with which that terminology is associated. The scope of the invention should therefore be construed in accordance with the appended claims and any equivalents thereof.

What is claimed is:

1. An apparatus comprising:
a bio-compatible carrier configured for implantation into a cavity to deliver radioactive energy from a radioactive seed embedded in the bio-compatible carrier to tissue around the cavity;
a loader having:
a loading bed between first and second surfaces of the loader, the loading bed sized to support the carrier on the loading bed;
a loading port defining a first alignment interface on an outer surface of the loader; and
an injection device having:
an injection channel configured to contain a radioactive seed;
a distal end having a second alignment interface adapted to engage with the first alignment interface of the loading port; and
a plunger having a first end comprising a longitudinal rod extending at least partially within the injection channel and a second end outside of the injection channel configured for engagement to move the longitudinal rod within the injection channel;
wherein with at least a portion of the injection device inserted into the loading port such that the first alignment interface engages the second alignment interface, the radioactive seed is movable out of the injection device into the bio-compatible carrier on the loading bed in response to movement of the second end of the plunger towards the distal end of the injection device.

2. The apparatus of claim 1, further comprising:
a punch configured to create a guide channel in the carrier at a location of the carrier where the radioactive seed is inserted.

3. The apparatus of claim 1, wherein the first and second alignment interfaces are non-linear and are shaped to engage one another such that the injection device is stabilized with reference to the loader when the first and second alignment interfaces are engaged.

4. The apparatus of claim 1, wherein the first and second alignment interfaces each include a single tier.

5. The apparatus of claim 1, wherein the first and second alignment interfaces each include two or more tiers.

6. The apparatus of claim 1, the loader further comprising:
a second loading port defining an additional alignment interface on the outer surface of the loader, the additional alignment interface also configured to engage with the second alignment interface of the injection device.

7. The apparatus of claim 1, wherein the loader further comprises a second loading port and the injection device includes a second injection channel, wherein when the first and second alignment interfaces are engaged the second injection channel is aligned with the second loading port such that said movement of the second end of the plunger towards the distal end of the injection device causes a second radioactive seed within the second injection channel to move through the second loading port and into the carrier.

8. A method comprising:
aligning a first alignment interface of a loading device with a second alignment interface of an injection device,
wherein the loading device comprises:
a loading bed sized to support a bio-compatible carrier, the bio-compatible carrier configured for delivery of radioactive energy from a radioactive seed embedded in the bio-compatible carrier to tissue; and a loading port defining the first alignment interface on an outer surface of the loading device; and moving the radioactive seed out of the injection device into the bio-compatible carrier on the loading bed in response to movement of a longitudinal rod of the injection device towards the bio-compatible carrier, wherein the injection device comprises:

an injection channel configured to support the radioactive seed;

the second alignment interface adapted to engage with the first alignment interface of the loading port; and a longitudinal rod extending at least partially within the injection channel and configured for engagement to thereby move the longitudinal rod within the injection channel.

9. The method of claim 8, further comprising:
creating a guide channel in the bio-compatible carrier at a location where the radioactive seed is to be inserted.

10. The method of claim 8, wherein the first and second alignment interfaces are non-linear and are shaped to engage one another such that the injection device is stabilized with reference to the loading device when the first and second alignment interfaces are engaged.

11. The method of claim 8, wherein the first and second alignment interfaces each include a single tier.

12. The method of claim 8, wherein the first and second alignment interfaces each include two or more tiers.

13. The method of claim 8, wherein the loading device further comprises an additional alignment interface on the outer surface of the loader, the additional alignment interface also configured to engage with the second alignment interface of the injection device.

14. The method of claim 8, wherein the loading device further comprises a second loading port and the injection device includes a second injection channel, wherein when the first and second alignment interfaces are engaged the second injection channel is aligned with the second loading port such that said movement of the longitudinal rod towards the bio-compatible carrier causes a second radioactive seed within the second injection channel to move through the second loading port and into the carrier.

15. The method of claim 8, wherein said aligning and moving are performed by automated equipment.

16. The method of claim 8, further comprising:
automatically loading the radioactive seed into the injection channel via a force-loaded magazine holding a plurality of radioactive seeds.

17. The method of claim 16, further comprising:
in response to moving the radioactive seed out of the injection device, automatically loading a second radioactive seed into the injection device via the force-loaded magazine.

* * * * *